(12) United States Patent
Hao et al.

(10) Patent No.: US 9,040,157 B2
(45) Date of Patent: May 26, 2015

(54) HOLLOW NANOPARTICLES AND NANOCOMPOSITES AND METHODS OF MAKING HOLLOW NANOPARTICLES AND NANOCOMPOSITES

(75) Inventors: Yaowu Hao, Grapevine, TX (US); Chien-Wen Huang, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 22 days.

(21) Appl. No.: 13/161,251

(22) Filed: Jun. 15, 2011

(65) Prior Publication Data

US 2011/0311822 A1    Dec. 22, 2011

Related U.S. Application Data

(60) Provisional application No. 61/355,364, filed on Jun. 16, 2010.

(51) Int. Cl.
| | |
|---|---|
| *B32B 15/02* | (2006.01) |
| *B05D 7/00* | (2006.01) |
| *B01J 13/02* | (2006.01) |
| *B32B 3/26* | (2006.01) |

(Continued)

(52) U.S. Cl.
CPC ............. *B01J 13/02* (2013.01); *A61K 49/0065* (2013.01); *A61K 49/0093* (2013.01); *A61K 49/183* (2013.01); *A61K 51/1251* (2013.01); *C09B 63/00* (2013.01); *B22F 1/0018* (2013.01); *B22F 1/025* (2013.01); *B22F 9/00* (2013.01); *B22F 2001/0029* (2013.01); *B82Y 30/00* (2013.01)

(58) Field of Classification Search
None
See application file for complete search history.

(56) References Cited

U.S. PATENT DOCUMENTS

2005/0056118 A1* 3/2005 Xia et al. ............... 75/330
2008/0021212 A1* 1/2008 Whiteford et al. ........... 540/472
(Continued)

FOREIGN PATENT DOCUMENTS

WO    WO 2008/018707 A1 *    2/2008

OTHER PUBLICATIONS

Chen et al, Facile Synthesis of Gold-Silver Nanocages with Controllable Pores on the Surface, Oct. 28, 2006, JACS, pp. 14776-14777.*
(Continued)

*Primary Examiner* — Randy Gulakowski
*Assistant Examiner* — Jeffrey Washville
(74) *Attorney, Agent, or Firm* — John P. Zimmer; Smith Moore Leatherwood LLP

(57) ABSTRACT

In one aspect, hollow nanoparticles are described herein. In some embodiments, a hollow nanoparticle comprises a metal shell and a cavity substantially defined by the shell, wherein the shell has a thickness greater than or equal to about 5 nm and the cavity has a curved surface. In another aspect, methods of making hollow nanoparticles are described herein. In some embodiments, a method of making hollow nanoparticles comprises forming a plurality of gas bubbles and forming a shell on the surface of at least one of the plurality of gas bubbles, wherein at least one of the gas bubbles is electrochemically generated. In another aspect, composite particles are described herein. In some embodiments, a composite particle comprises at least one nanoparticle and a polycrystalline metal shell substantially encapsulating at least one nanoparticle, wherein at least one surface of at least one nanoparticle is not in contact with the shell.

15 Claims, 17 Drawing Sheets

(51) Int. Cl.

| | |
|---|---|
| A61K 49/00 | (2006.01) |
| A61K 49/18 | (2006.01) |
| A61K 51/12 | (2006.01) |
| C09B 63/00 | (2006.01) |
| B22F 1/00 | (2006.01) |
| B22F 1/02 | (2006.01) |
| B22F 9/00 | (2006.01) |
| B82Y 30/00 | (2011.01) |

(56) References Cited

U.S. PATENT DOCUMENTS

2008/0305489 A1* 12/2008 Thomas et al. .................. 435/6
2010/0228237 A1* 9/2010 Chung et al. .................. 606/13

OTHER PUBLICATIONS

Agrawal, Abhinandan et al., "Controlling the Location and Spatial Extent of Nanobubbles Using Hydrophobically Nanopatterned Surfaces," copyright 2005, American Chemical Society, NANO Letters 2005, vol. 5, No. 9, pp. 1751-1756.

Averitt, R.D et al., "Plasmon Resonance Shifts of Au-Coated Au2S Nanoshells: Insight Into Multicomponent Nanoparticle Growth," copyright 1997, The American Physical Review Letters, vol. 78, No. 22, Jun. 2, 1997, pp. 4217-4220.

Averitt, Richard D. et al., "Linear Optical Properties of Gold Nanoshells," copyright 1999, Optical Society of America, J. Opt. Soc. Am. B., vol. 16, No. 10, Oct. 1999, pp. 1824-1832.

Banholzer, Matthew J. et al., "Electrochemical Approach to and the Physical Consequences of Preparing Nanostructures from Gold Nanorods With Smooth Ends," copyright 2008, American Chemical Society, J. Phys. Chem., vol. 112, pp. 15729-15734.

Boisselier, Elodie et al., "Gold Nanoparticles in Nanomedicine: Preparations, Imaging, Diagnostics, Therapies and Toxicity," copyright 2009, The Royal Society fo Chemistry, Chem. Soc. Rev., vol. 38, pp. 1759-1782.

Borkent, Bram M. et al., "Superstability of Surface Nanobubbles," copyright 2007, The American Physical Society, PRL, vol. 98, pp. 204502-1-204502-4.

Brenner, Michael P. et al., "Dynamic Equilibrium Mechanism for Surface Nanobubble Stabilization," copyright 2008, The American Physical Society, PRL, vol. 101, pp. 214505-1-214505-4.

Cao, Huaqiang et al., "Generation and Growth Mechanism of Metal (Fe, Co, Ni) Nanotube Arrays," copyright 2006, Wiley-VCH Verlag GmbH & Co. KgaA, Winheim, ChemPhysChem, vol. 7, pp. 1500-1504.

Chen, Jingyi et al., "Gold Nanocages: Bioconjugation and Their Potential Use as Optical Imaging Contrast Agents," copyright 2005, American Chemical Society, Nano Letters 2005, vol. 5, No. 3, pp. 473-477.

Chiang, I-Chen et al., "Synthesis of Monodisperse FeAu Nanoparticles with Tunable Magnetic and Optical Properties," copyright 2007, Wiley-VCH Verlag GmbH & Co. KgaA, Weinheim, Advanced Functional Materials, vol. 17, pp. 1311-1316.

Choi, Jin-sil et al., "A Hybrid Nanoparticle Probe for Dual-Modality Positron Emission Tomography and Magnetic Resonance Imaging," copyright 2008, Wiley-VCH Verlag GmbH & Co. KgaA, Weinheim, Angew. Chem. Int. Ed., vol. 47, pp. 6259-6262.

Cole, Joseph R. et al., "Photothermal Efficiencies of Nanoshells and Nanorods for Clinical Therapeutic Applications," copyright 2009, American Chemical Society, J. Phys. Chem., vol. 113, pp. 12090-12094.

Cuenca, Alex G. et al., "Emerging Implications of Nanotechnology on Cancer Diagnostics and Therapeutics," copyright 2006, American Cancer Society, Wiley InterScience; pp. 459-466.

Daniel, Marie-Christine et al., "Gold Nanoparticles: Assembly, Supramolecular Chemistry, Quantum-Size-Related Properties, and Applications Toward Biology, Catalysis, and Nanotechnology," copyright 2004, American Chemical Society, Chem. Rev., vol. 104, pp. 293-346.

Davis, Mark E. et al., "Nanoparticle Therapeutics: An Emerging Treatment Modality for Cancer," copyright 2008 Macmillan Publishers Limited, Nature Reviews, vol. 7, pp. 771-782.

Devoisselle, Jean-Marie et al., "Magnetic Nanoparticles and Their Applications in Medicine," copyright 2006, Nanomedicine, 1.2, pp. 1-17.

Ferrari, Mauro, "Cancer Nanotechnology: Opportunities and Challenges," copyright 2005, Nature Publishing Group, Nature Reviews, vol. 5, pp. 161-171.

Fu, Kun et al., "Measurement of Immunotargeted Plasmonic Nanoparticles' Cellular Binding: A Key Factor in Optimizing Diagnostic Efficacy," copyright 2008, IOP Publishing Ltd., Nanotechnology, vol. 19, pp. 1-6.

Gabe, D.R., "The Role of Hydrogen in Metal Electrodeposition Processes," copyright 1997, Chapman & Hall, Journal of Applied Electrochemistry, vol. 27, pp. 908-915.

Gobin, André M. et al., "Near-Infrared Resonant Nanoshells for Combined Optical Imaging and Photothermal Cancer Therapy," copyright 2007, American Chemical Society, NANO Letters 2007, Vol. 7, No. 7, pp. 1929-1934.

Groman, Ernest V. et al., "Ultrasmall Mixed Ferrite Colloids as Multidimensional Magnetic Resonance Imaging, Cell Labeling, and Cell Sorting Agents," copyright 2007, American Chemical Society, Bioconjugate Chem., vol. 18, pp. 1763-1771.

Grzelczak, Marek et al., "Shape Control in Gold Nanoparticle Synthesis," copyright 2008, The Royal Socity of Chemistry, Chem. Soc. Rev., vol. 37, pp. 1783-1791.

Hirsch, L.R. et al., "Nanoshell-Mediated Near-Infrared Thermal Therapy of Tumors Under Magnetic Resonance Guidance," copyright 2003, The National Academy of Sciences of the USA, PNAS, vol. 100, No. 23, pp. 13549-13554.

Issa, Nader A. et al., "Optical Nanofocusing on Tapered Metallic Waveguides," copyright 2006, Springer Science, Plasmonics, vol. 2, pp. 31-37.

Jain, Prashant K. et al, Erratum re: Fig. 6, copyright 2007, Nanotoday, Apr. 2007, vol. 2, No. 2, p. 16.

Jana, Nikhil R. et al., "Wet Chemical Synthesis of High Aspect Ratio Cylindrical Gold Nanorods," copyright 2001, American Chemical Society, J. Phys. Chem. B, vol. 105, pp. 4065-4067.

Johnson, P.B. et al., "Optical Constants of the Noble Metals," copyright 1972, Physical Review, vol. 6, No. 12., pp. 4370-4379.

Keren, S. et al., "Noninvasive Molecular Imaging of Small Living Subjects Using Raman Spectroscopy," copyright 2008, The National Academy of Science, PNAS, vol. 105, No. 15, pp. 5844-5849.

Lal, Surbhi et al., "Nanoshell-Enabled Photothermal Cancer Therapy: Impending Clinical Impact," copyright 2008, Accounts of Chemical Research, vol. 41, No. 12, pp. 1842-1851.

Lal, Surbhi et al., "Tailoring Plasmonic Substrates for Surface Enhanced Spectroscopies," copyright 2008, Chem. Soc. Rev., vol. 37, pp. 898-911.

Lee, Ha-Young et al., "PET/MRI Dual-Modality Tumor Imaging Using Arginine-Glycerine-Aspartic (RGD)—Conjugated Radiolabeled Iron Oxide Nanoparticles," copyright 2008, Society of Nuclear Medicine, The Journal of Nuclear Medicine, vol. 49, No. 8, pp. 1371-1379.

Levin, Carly S. et al., "Magnetic-Plasmonic Core-Shell Nanoparticles," copyright 2009, American Chemical Society, ACS Nano, vol. 3, No. 6, pp. 1379-1388.

Merchant, B., "Gold, the Noble Metal and the Paradoxes of Its Toxicology," copyright 1998, The International Association of Biological Standardization, Biologicals, vol. 26, pp. 49-59.

Merrill, E.W. et al., "Platelet-Compatible Hydrophilic Segmented Polyurethanes From Polyethylene Glycols and Coclohexane Diisocyanate," copyright 1982, Trans. Am. Soc. Artif. Intern. Organs, vol. 28, pp. 482-487.

Millstone, Jill E. et al., "Observation of a Quadruple Plasmon Mode for a Colloidal Solution of Gold Nanoprisms," copyright 2005, J. Am. Chem. Soc., vol. 127, pp. 5312-5313.

Moghimi, S.M. et al., "Coating Particles With a Block Co-Polymer (Poloxamine-908) Suppresses Opsonization but Permits the Activity of Dysopsonins in the Serum," copyright 1993, Elsevier Science Publishers B.V., Biochimica et Biophysica Acta, vol. 1179, pp. 157-165.

(56) References Cited

OTHER PUBLICATIONS

Neeves, A.E. et al., "Composite Structures for the Enhancement of Nonlinear-Optical Susceptibility," copyright 1989, Optical Society of America, J. Opt. Soc. Am. B, vol. 6, No. 4, pp. 787-796.
Nie, Shuming et al., "Nanotechnology Applications in Cancer," copyright 2007, The Annual Review of Biomedical Engineering, vol. 9, pp. 257-288.
O'Donoghue, Meghan B. et al., "Nanoparticles for Multiplex Diagnostics and Imaging," copyright 2006, Nanomedicine, 1.4, pp. 1-17.
Paciotti, Giulio F. et al., "Colloidal Gold Nanoparticles: A Novel Nanoparticle Platform for Developing Multifunctional Tumor-Targeted Drug Delivery Vectors," copyright 2006, Wiley-Liss, Inc., Drug Development Research, vol. 67, pp. 47-54.
Paciotti, Giulio F. et al., "Colloidal Gold: A Novel Nanoparticle Vactor for Tumor Directed Drug Delivery," copyright 2004, Taylor & Francis, Inc., Drug Delivery, vol. 11, pp. 169-183.
Papahadjopoulos, D. et al., "Sterically Stabilized Liposomes: Improvements in Pharmacokinetics and Antitumor Therapeutic Efficacy," copyright 1991, Proc. Natl. Acad. Sci. USA, vol. 88, pp. 11460-11464.
Perrault, Steven D. et al., "Mediating Tumor Targeting Efficiency of Nanoparticles Through Design," copyright 2009, American Chemical Society, Nano Letters 2009, vol. 9, No. 5, pp. 1909-1915.
Porter, Marc D. et al., "SERS as a Bioassay Platform: Fundamentals, Design, and Applications," copyright 2008, The Royal Society of Chemistry, Chem. Soc. Review, vol. 37, pp. 1001-1011.
Prodan, E. et al., "A Hybridization Model for the Plasmon Response of Complex Nanostructures," copyright 2003, Science, vol. 302, pp. 419-422.
Qian, Ximei et al., "In Vivo Tumor Targeting and Spectroscopic Detection With Surface-Enhanced Raman Nanoparticle Tags," copyright 2008, Nature Biotechnology, vol. 26, No. 1, pp. 83-90.
Radloff, Corey et al., "Plasmonic Properties of Concentric Nanoshells," copyright 2004, American Chemical Society, Nano Letters 2004, vol. 4, No. 7, pp. 1323-1327.
Rauscher, M. et al., "Wetting Phenomena in Nanofluids," copyright 2008, The Annual Review of Materials Research, vol. 38, pp. 143-172.
Rodriguez-Fernandez, Jessica et al., "The Effect of Surface Roughness on the Plasmonic Response of Individual Sub-Micron Gold Spheres," copyright 2009, The Owner Societies, Physical Chemistry Chemical Physics, vol. 11, pp. 5909-5914.
Tyrrell, James W.G. et al., "Images of Nanobubbles on Hydrophobic Surfaces and Their Interactions," copyright 2001, The American Physical Society, Physical Review Letters, vol. 87, No. 17, pp. 176104-1-176104-4.
Wang, H. et al., "Light Scattering From Spherical Plasmonic Nanoantennas: Effects of Nanoscale Roughness," copyright 2006, Springer-Verlag, Appl. Phys. B, vol. 84, pp. 191-195.
Wang, Hui et al,. "Mesoscopic Au 'Meatball' Particles," copyright 2008, Wiley-VCH Verlag GmbH & Co. KgaA, Adv. Mater., vol. 20, pp. 820-825.
Wang, Qingtao et al., "Controllable Template Synthesis of Ni/Cu Nanocable and Ni Nanotube Arrays: A One-Step Coelectrodeposition and Electrochemical Etching Method," copyright 2005, American Chemical Society, J. Phys. Chem. B, vol. 109, pp. 23326-23329.
Wu, Yanpeng et al., "Plasmon Hybridization in Nanoshells With a Nonconentric Core," copyright 2006, American Institute of Physics, The Journal of American Physics, vol. 125, pp. 144708-1-124708-10.
Xiao, Ming et al., "Gold Nanotags for Combined Multi-Colored Raman Spectroscopy and X-Ray Computed Tomography," copyright 2010, IOP Publishing Ltd., Nanotechnology, vol. 21, pp. 1-8.
Xu, Zhichuan et al., "Magnetic Core/Shell $Fe_3O_4$/Au/Ag Nanoparticles With Tunable Plasmonic Properties," copyright 2007, J. Am. Chem. Soc., vol. 129, pp. 8698-8699.
Yang, Shangjiong et al., "Characterization of Nanobubbles on Hydroponic Surfaces in Water," copyright 2007, American Chemical Society, Langmuir, vol. 23, pp. 7072-7077.
Yavuz, Mustafa S. et al., "Gold Nanocages Covered by Smart Polymers for Controlled Release With Near-Infrared Light," copyright 2009, Nature Materials, vol. 8, pp. 935-939.
Yu, Kefeng et al., "Morphologies and Surface Plasmon Resonance Properties of Monodisperse Bumpy Gold Nanoparticles," copyright 2008, American Chemical Society, Langmuir, vol. 24, pp. 5849-5854.
Yu, Kyeong Nam et al., "Multiplex Targeting, Tracking, and Imaging of Apoptosis by Fluorescent Surface Enhanced Raman Spectroscopic Dots," copyright 2007, American Chemical Society, Bioconjugate Chem., vol. 18, pp. 1155-1162.
Zhang, Lijuan et al., "Electrochemically Controlled Formation and Growth of Hydrogen Nanobubbles," copyright 2006, American Chemical Society, Langmuir, vol. 22, pp. 8109-8113.

\* cited by examiner (A) Cell  (B) Enlargement (A) Cell  (B) Enlargement  (C) SEM (A) Top  (B) Cross Section Branches Branches (A) Mask    (B) Patterned Substrate (A)          (B)

HOLLOW NANOPARTICLES AND NANOCOMPOSITES AND METHODS OF MAKING HOLLOW NANOPARTICLES AND NANOCOMPOSITES

CROSS-REFERENCE TO RELATED APPLICATIONS

This application claims priority pursuant to 35 U.S.C. §119 (e) to U.S. Provisional Patent Application Ser. No. 61/355,364, filed on Jun. 16, 2010, which is hereby incorporated by reference in its entirety.

STATEMENT REGARDING FEDERALLY SPONSORED RESEARCH

This invention was made with government support under contract ECCS-0901849 awarded by the National Science Foundation. The government has certain rights in the invention.

FIELD OF THE INVENTION

The present invention relates to nanoparticles and nanocomposites and methods of making and using nanoparticles and nanocomposites.

BACKGROUND

Nanoparticles and nanocomposites comprising nanoparticles can be used in a variety of applications. Therefore, nanocomposites and nanoparticles having various structures and properties are desired. Methods of making nanoparticles and nanocomposites comprising nanoparticles are also desired.

SUMMARY

In one aspect, hollow nanoparticles are described herein. A hollow nanoparticle described herein, in some embodiments, comprises a metal shell and a cavity substantially defined by the shell, wherein the shell has a thickness greater than or equal to about 5 nm and the cavity has a curved surface. In some embodiments, a hollow nanoparticle comprises a polycrystalline metal shell and a cavity substantially defined by the shell, wherein the cavity has a curved surface. In some embodiments, the cavity has a diameter of about 50 nm to about 300 nm. In some embodiments, the nanoparticle has a surface roughness between about 3 nm and about 8 nm. In some embodiments, the nanoparticle exhibits a surface plasmon resonance (SPR) peak between about 600 nm and about 900 nm. In some embodiments, the cavity has dispersed therein one or more magnetic nanoparticles.

In another aspect, methods of making hollow nanoparticles are described herein. A method of making hollow nanoparticles described herein, in some embodiments, comprises forming a plurality of gas bubbles and forming a shell on the surface of at least one of the plurality of gas bubbles, wherein at least one of the gas bubbles is electrochemically generated. In some embodiments, the shell is a metal shell. In some embodiments, at least one of the gas bubbles on which a shell is formed has a diameter between about 40 nm and about 60 nm.

In some embodiments, a method of making hollow nanoparticles comprises forming a plurality of gas bubbles, forming a shell on the surface of at least one of the plurality of gas bubbles, providing one or more precursors of a second nanoparticle, and forming the second nanoparticle from the one or more precursors within a cavity defined by the shell, wherein at least one of the gas bubbles is electrochemically generated. In some embodiments, a method described herein is a one-pot method.

In another aspect, composite particles are described herein. A composite particle described herein, in some embodiments, comprises at least one nanoparticle and a metal shell substantially encapsulating at least one nanoparticle, wherein the metal shell has a thickness of about 10 nm to about 200 nm and at least one surface of at least one nanoparticle is not in contact with the shell. In some embodiments, no surface of any nanoparticle is in contact with the shell. In some embodiments, a composite particle described herein comprises a plurality of nanoparticles and a metal shell substantially encapsulating the plurality of nanoparticles, wherein the metal shell has a thickness of about 10 nm to about 200 nm and at least one surface of at least one nanoparticle is not in contact with the shell. In some embodiments, no surface of any nanoparticle is in contact with the shell.

In some embodiments, a composite particle comprises at least one nanoparticle and a polycrystalline metal shell substantially encapsulating at least one nanoparticle, wherein at least one surface of at least one nanoparticle is not in contact with the shell. In some embodiments of composite particles described herein, no surface of at least one nanoparticle is in contact with the shell. In some embodiments, no surface of any nanoparticle is in contact with the shell. In some embodiments, at least one nanoparticle comprises a magnetic nanoparticle.

In another aspect, methods of making a composite particle are described herein. A method of making a composite particle described herein, in some embodiments, comprises providing a porous hollow nanoparticle, providing one or more precursors of at least one second nanoparticle, mixing the one or more precursors with the hollow nanoparticle, and forming at least one second nanoparticle from the one or more precursors within the hollow nanoparticle. In some embodiments, a method of making a composite particle comprises providing a porous hollow nanoparticle, providing one or more precursors of at least one second nanoparticle, mixing the one or more precursors with the hollow nanoparticle, forming at least one second nanoparticle from the one or more precursors within the hollow nanoparticle, and sealing the porous hollow nanoparticle. In some embodiments, a method described herein is a one-pot method.

In some embodiments, a method of making a composite particle comprises providing a porous hollow nanoparticle, providing one or more therapeutic agents, and mixing the one or more therapeutic agents with the hollow nanoparticle to dispose at least one of the therapeutic agents within the hollow nanoparticle. In some embodiments, a method of making a composite particle comprises providing a hollow nanoparticle, providing one or more Raman active species, and mixing the one or more active Raman species with the hollow nanoparticle to associate at least one of the Raman active species with an outer surface of the composite particle. In some embodiments, a method described herein is a one-pot method.

In another aspect, methods of imaging and treating biological environments are disclosed herein. A method of imaging a biological environment described herein, in some embodiments, comprises providing a hollow nanoparticle described herein and irradiating the hollow nanoparticle with electromagnetic radiation. A method of treating a biological environment described herein, in some embodiments, comprises providing a hollow nanoparticle described herein and irradiating the hollow nanoparticle with electromagnetic radiation. In some embodiments, both imaging and treating a biological environment can be carried out at substantially the same time. In some embodiments, at least a portion of the electromagnetic radiation is inelastically scattered by the hollow nanoparticle. In some embodiments, at least a portion of the electromagnetic radiation interacts with a surface plasmon of the hollow nanoparticle. In some embodiments, irradiating induces photothermal heating. In some embodiments, irradiating induces rupturing of the hollow nanoparticle. In some embodiments, imaging a biological environment comprises imaging with surface plasmon resonance (SPR) imaging. In some embodiments, imaging a biological environment comprises imaging with surface enhanced Raman spectroscopy (SERS). In some embodiments, imaging a biological environment comprises imaging with magnetic resonance imaging (MRI). In some embodiments, imaging a biological environment comprises imaging with positron emission tomography (PET). In some embodiments, imaging a biological environment comprises imaging with a combination of two or more of SPR imaging, SERS, MRI, and PET. In some embodiments, treating a biological environment comprises treating cancer.

In another aspect, methods of delivering a payload are described herein. A method of delivering a payload described herein, in some embodiments, comprises providing a hollow nanoparticle comprising a shell, a cavity substantially defined by the shell, and a payload within the cavity; and releasing the payload. In some embodiments, the payload is provided within the cavity by diffusion. In some embodiments, releasing the payload comprises rupturing the shell.

In another aspect, methods of selectively depositing hollow nanoparticles on a surface are described herein. A method of selectively depositing hollow nanoparticles on a surface, in some embodiments, comprises providing a substrate having a plurality of domains with differing hydrophobicity, forming a plurality of gas bubbles, and forming a shell on the surface of at least one of the plurality of gas bubbles to form a hollow nanoparticle. In some embodiments, forming a shell comprises forming a metal shell.

These and other embodiments are described in greater detail in the detailed description and examples which follow.

DETAILED DESCRIPTION

Figure 1:
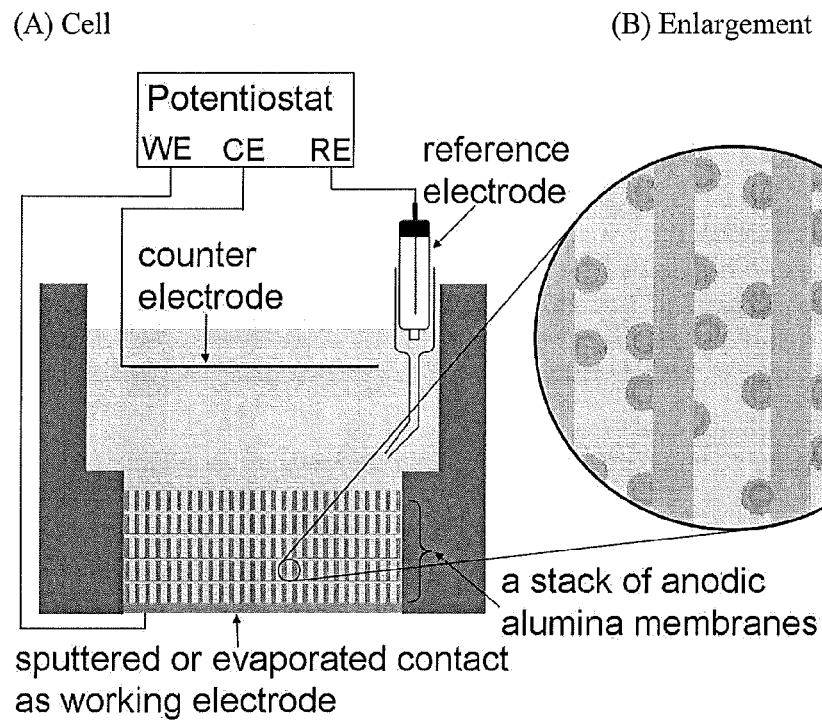
FIG. 1A illustrates a three-electrode cell suitable for use in some methods described herein.
FIG. 1B is an enlarged view of several channels in a stacked membrane in the cell of FIG. 1A.

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

Embodiments described herein can be understood more readily by reference to the following detailed description and examples and their previous and following descriptions. Elements, apparatus, and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In one aspect, hollow nanoparticles are described herein which, in some embodiments, may offer one or more advantages over prior nanoparticles. In some embodiments, for example, a hollow nanoparticle described herein exhibits an SPR peak tunable from about 600 nm to about 900 nm, thereby providing properties useful in various imaging, therapeutic, theranostic, and sensing applications. In some embodiments, a hollow nanoparticle described herein exhibits desirable magnetic and/or photothermal properties. In some embodiments, a hollow nanoparticle described herein is useful for magnetic resonance imaging (MRI) and positron emission tomography (PET). In some embodiments, a hollow nanoparticle described herein exhibits desirable catalytic properties. In some embodiments, a hollow nanoparticle described herein is non-toxic. In some embodiments, a hollow nanoparticle described herein is operable for photothermal therapy.

In some embodiments, a hollow metal nanoparticle comprises a metal shell and a cavity substantially defined by the shell, wherein the shell has a thickness greater than or equal to about 5 nm and the cavity has a curved surface. In some embodiments, a hollow metal nanoparticle comprises a metallic shell and a cavity substantially defined by the shell, wherein the shell has a thickness greater than or equal to about 5 nm and the cavity has a curved surface. In some embodiments, a hollow nanoparticle comprises a polycrystalline metal shell and a cavity substantially defined by the shell, wherein the cavity has a curved surface. In some embodiments, a hollow nanoparticle comprises a polycrystalline metallic shell and a cavity substantially defined by the shell, wherein the cavity has a curved surface.

Hollow metal nanoparticles described herein, in some embodiments, have a cavity exhibiting various morphologies. In some embodiments, for example, the cavity is substantially spherical or hemispherical. In some embodiments, the cavity is substantially parabolic, elliptical, or ellipsoidal. In some embodiments, the cavity comprises a polygonal or faceted surface. The cavity, in some embodiments, exhibits various sizes. In some embodiments, the cavity has a diameter of about 50 nm to about 300 nm. In some embodiments, the cavity has a diameter of about 50 nm.

Hollow metal nanoparticles described herein, in some embodiments, exhibit various morphologies. In some embodiments, a hollow metal nanoparticle described herein is substantially hemispherical. In some embodiments, the nanoparticle is substantially tubular. In some embodiments, the nanoparticle comprises a curved exterior surface. In some embodiments, the nanoparticle is substantially spherical. In some embodiments, the nanoparticle comprises a parabolic exterior surface. In some embodiments, the nanoparticle is substantially elliptical or ellipsoidal.

Hollow metal nanoparticles described herein, in some embodiments, have various sizes. In some embodiments, a hollow metal nanoparticle comprising a metal shell and a cavity substantially defined by the shell has a diameter of about 50 nm to about 1000 nm. In some embodiments, the hollow nanoparticle has a diameter of about 50 nm to about 160 nm, about 60 nm to about 160 nm, about 80 nm to about 160 nm, or about 100 nm to about 150 nm. In some embodiments, the hollow nanoparticle has a diameter of about 60 nm to about 100 nm.

In some embodiments, a substantially tubular hollow nanoparticle has a diameter ranging from about 100 nm to about 400 nm and a length ranging from about 500 nm to about 2 μm. In some embodiments, a substantially tubular hollow nanoparticle has a length of about 1 μm.

In some embodiments, a plurality of hollow nanoparticles described herein has a narrow size distribution. In some embodiments, a plurality of hollow nanoparticles described herein has a size distribution with a standard deviation not greater than about 20%. In some embodiments, a plurality of hollow nanoparticles described herein has a size distribution with a standard deviation not greater than about 15%, not greater than about 10%, or not greater than about 5%. In some embodiments, a plurality of hollow nanoparticles described herein has a size distribution of 106 nm±10 nm, wherein 106 nm is the mean diameter and 10 nm is the standard deviation.

Hollow metal nanoparticles described herein, in some embodiments, exhibit various shell structures. In some embodiments, a shell of a hollow metal nanoparticle is porous. In some embodiments, for example, the shell has pores having a size between about 0.5 nm and about 3 nm. In some embodiments, the shell has pores having a size between about 2 nm and about 3 nm. In some embodiments, the shell of a hollow metal nanoparticle is non-porous. In some embodiments, the shell is polycrystalline. In some embodiments, the shell has a grain size of about 3 nm to about 8 nm. In some embodiments, the shell has a grain size of about 5 nm to about 8 nm. In some embodiments, the shell has a grain size less than about 5 nm. In some embodiments, the shell is single crystalline.

Hollow metal nanoparticles described herein, in some embodiments, exhibit various shell thicknesses. In some embodiments, a shell of a hollow metal nanoparticle has a thickness of about 5 nm to about 1000 nm. In some embodiments, the shell has a thickness greater than about 20 nm. In some embodiments, the shell has a thickness of about 5 nm to about 8 nm. In some embodiments, the shell has a thickness of about 5 nm to about 20 nm, about 8 nm to about 25 nm, about 8 nm to about 45 nm, about 25 nm to about 45 nm, about 25 nm to about 500 nm, about 25 nm to about 1000 nm, about 45 nm to about 300 nm, about 45 nm to about 500 nm, or about 45 nm to about 1000 nm.

Hollow metal nanoparticles described herein, in some embodiments, exhibit various surface roughnesses. In some embodiments, surface roughness values described herein are based on the grain size of the surface measured by HR-TEM. In some embodiments, for example, a surface roughness of about 5 nm corresponds to a measured grain size of about 5 nm. In some embodiments, a hollow metal nanoparticle described herein has a surface roughness less than about 5 nm. In some embodiments, a nanoparticle has a surface roughness between about 3 nm and about 8 nm. In some embodiments, a nanoparticle has a surface roughness of about 5 nm to about 8 nm. In some embodiments, a nanoparticle has a surface roughness less than about 3 nm or more than about 8 nm.

Hollow metal nanoparticles described herein, in some embodiments, comprise shells having various compositions. In some embodiments, for example, the shell of a hollow metal nanoparticle described herein comprises one or more of iron (Fe), cobalt (Co), nickel (Ni), palladium (Pd), platinum (Pt), copper (Cu), silver (Ag), gold (Au), zinc (Zn), and tin (Sn). In some embodiments, the shell comprises Au. In some embodiments, the shell comprises a metal capable of undergoing deposition by an oxidation-reduction reaction. In some embodiments, the shell comprises a metal capable of undergoing electroless deposition. In some embodiments, the shell comprises a plurality of metals having substantially similar reduction potentials.

Hollow metal nanoparticles described herein, in some embodiments, exhibit various optical properties. In some embodiments, a hollow metal nanoparticle described herein exhibits an absorption profile comprising a surface plasmon resonance (SPR) peak. In some embodiments, for example, a hollow metal nanoparticle comprising a metal shell described herein exhibits a surface plasmon resonance peak between about 600 nm and about 900 nm. In some embodiments, the nanoparticle exhibits a surface plasmon resonance peak between about 600 nm and about 750 nm. In some embodiments, the nanoparticle exhibits a surface plasmon resonance peak between about 650 nm and about 900 nm. In some embodiments, the nanoparticle exhibits a surface plasmon resonance peak between about 700 nm and about 800 nm Hollow nanoparticles described herein, in some embodiments, comprise various materials within the cavity defined by the metal shell. Any material not incompatible with the objectives of the present invention may be used in some embodiments. In some embodiments, the cavity comprises one or more of a gas, a nanoparticle, a therapeutic agent, an enzyme, a catalyst, and a dye. In some embodiments, the cavity comprises a gas. In some embodiments, the gas comprises a reducing gas. In some embodiments, the reducing gas is capable of reducing one or more of the metals from a higher oxidation state to a lower oxidation state. In some embodiments, the reducing gas is capable of reducing one or more of the metals from a positive oxidation state to an oxidation state of zero. In some embodiments, for example, the gas comprises $H_2$. In some embodiments, the gas comprises $NH_3$. In some embodiments, the gas comprises an electrochemically generated gas.

In some embodiments, a hollow metal nanoparticle described herein further comprises one or more additional nanoparticles at least partially disposed in the cavity defined by the metal shell. In some embodiments, a hollow metal nanoparticle described herein further comprises a plurality of second nanoparticles at least partially disposed in the cavity defined by the metal shell. In some embodiments, a hollow metal nanoparticle described herein further comprises at least one second nanoparticle at least partially disposed in the cavity defined by the metal shell. In some embodiments, at least one second nanoparticle comprises a cluster of nanoparticles. In some embodiments, at least one second nanoparticle comprises an organic nanoparticle. In some embodiments, at least one second nanoparticle comprises an inorganic nanoparticle. In some embodiments, at least one second nanoparticle comprises a semiconductor nanoparticle. In some embodiments, the second nanoparticle comprises a metal nanoparticle. In some embodiments, at least one second nanoparticle comprises a metal oxide nanoparticle. In some embodiments, at least one second nanoparticle comprises a ceramic nanoparticle. In some embodiments, at least one second nanoparticle comprises a quantum dot. In some embodiments, at least one second nanoparticle comprises a magnetic nanoparticle. In some embodiments, the magnetic nanoparticle is superparamagnetic. In some embodiments, the magnetic nanoparticle is ferromagnetic.

In some embodiments, at least one second nanoparticle can demonstrate various compositions. In some embodiments, at least one second nanoparticle comprises iron oxide. In some embodiments, at least one second nanoparticle comprises doped $Fe_3O_4$. In some embodiments, doped $Fe_3O_4$ comprises one or more nuclides useful for positron emission tomography (PET). In some embodiments, doped $Fe_3O_4$ comprises one or more of $^{64}Cu$, $^{89}Zr$, $^{11}C$, $^{18}F$, and $^{67}Ga$. In some embodiments, doped $Fe_3O_4$ comprises one or more of $^{64}Cu$ and $^{89}Zr$.

In some embodiments, at least one second nanoparticle comprises a second hollow metal nanoparticle. In some embodiments, the second hollow metal nanoparticle has substantially the same chemical composition as the shell.

In some embodiments wherein the hollow metal nanoparticle comprises at least one second nanoparticle, at least one second nanoparticle has a diameter of less than about 50 nm. In some embodiments, at least one second nanoparticle has a diameter of less than about 20 nm. In some embodiments, at least one second nanoparticle has a diameter between about 5 nm and about 20 nm or between about 30 nm and about 50 nm. In some embodiments, the shell is porous and at least one second nanoparticle has a diameter greater than the pore size.

In some embodiments, the cavity of a hollow metal nanoparticle described herein comprises a therapeutic agent. In some embodiments, the therapeutic agent comprises a gas. In some embodiments, the therapeutic agent comprises an aqueous solution. In some embodiments, the therapeutic agent comprises a drug.

Hollow metal nanoparticles described herein, in some embodiments, further comprise various species associated with one or more outer surfaces of the nanoparticle. In some embodiments, one or more species are associated with an outer surface directly. In some embodiments, one or more species are associated with an outer surface indirectly. In some embodiments, one or more species are associated with an outer surface indirectly through one or more species that are associated with an outer surface directly. In some embodiments, at least one species associated with an outer surface comprises a targeting agent. In some embodiments, at least one species associated with an outer surface comprises a Raman active species. In some embodiments, at least one species associated with an outer surface comprises a polyethylene glycol moiety. In some embodiments, a first species associated with an outer surface comprises a Raman active species and forms a first layer and a second species associated with the outer surface comprises a polyethylene glycol moiety and forms a second layer, wherein the second layer substantially surrounds the first layer. In some embodiments, a first species associated with an outer surface comprises a polyethylene glycol moiety and a second species associated with the outer surface comprises a targeting agent.

In another aspect, methods of making hollow nanoparticles are described herein, which, in some embodiments, may offer one or more advantages over prior methods of making nanoparticles. In some embodiments, for example, a method of making hollow nanoparticles described herein is simple, efficient, scalable, inexpensive, and reproducible. In some embodiments, a method of making hollow nanoparticles comprises forming a plurality of gas bubbles and forming a shell on the surface of at least one of the plurality of gas bubbles to form a hollow nanoparticle, wherein at least one of the gas bubbles is electrochemically generated. In some embodiments, forming a plurality of gas bubbles comprises electrochemically forming a plurality of gas bubbles. In some embodiments, forming a shell on the surface of at least one of the plurality of gas bubbles to form a hollow nanoparticle comprises forming a shell on the surface of at least one electrochemically generated gas bubble. In some embodiments, the shell is metallic.

Methods of making hollow nanoparticles described herein, in some embodiments, comprise forming a plurality of gas bubbles having various physical and chemical properties. In some embodiments, at least one of the gas bubbles comprises a reducing gas. In some embodiments, at least one of the gas bubbles comprises $H_2$. In some embodiments, at least one of the gas bubbles comprises $NH_3$. In some embodiments, at least one of the gas bubbles comprises an oxidizing gas. In some embodiments, at least one of the gas bubbles comprises $O_2$. In some embodiments, at least one of the gas bubbles comprises a relatively inert gas. In some embodiments, at least one of the gas bubbles comprises $CO_2$.

In some embodiments, a method of making hollow nanoparticles described herein comprises forming a shell on at least one gas bubble having various sizes. In some embodiments, for example, at least one of the gas bubbles on which a shell is formed has a diameter between about 40 nm and about 60 nm. In some embodiments, at least one of the gas bubbles on which a shell is formed has a diameter between about 50 nm and about 300 nm. In some embodiments, at least one of the gas bubbles on which a shell is formed has a diameter of about 50 nm.

Methods of making hollow nanoparticles described herein, in some embodiments, comprise forming at least one gas bubble electrochemically at various applied potentials. In some embodiments, at least one of the gas bubbles is electrochemically generated at a potential more negative than the equilibrium potential. In some embodiments, at least one of the gas bubbles is electrochemically generated at a potential more negative than the equilibrium potential of gas evolution. In some embodiments, for example, at least one of the gas bubbles is electrochemically generated at a potential more negative than about −0.6 V relative to Ag/AgCl. In some embodiments, at least one of the gas bubbles is electrochemically generated at a potential between about −0.7 V and −0.85 V relative to Ag/AgCl. In some embodiments, at least one of the gas bubbles is electrochemically generated at a potential between about −0.55 V and −0.8 V relative to Ag/AgCl. In some embodiments, at least one of the gas bubbles is electrochemically generated at a potential more negative than about −0.6 V relative to Ag/AgCl at about 25° C. and a pH between about 5 and about 8. In some embodiments, at least one of the gas bubbles is electrochemically generated at a potential between about −0.7 V and −0.85 V relative to Ag/AgCl at about 25° C. and a pH between about 5 and about 8. In some embodiments, at least one of the gas bubbles is electrochemically generated at a potential between about −0.55 V and −0.8 V relative to Ag/AgCl at about 25° C. and a pH between about 5 and about 8.

In some embodiments, a method of making hollow nanoparticles comprises forming a plurality of gas bubbles and forming a shell on the surface of at least one of the plurality of gas bubbles to form a hollow nanoparticle, wherein at least one of the gas bubbles is electrochemically generated and wherein forming a shell comprises depositing material through one or more oxidation-reduction reactions. In some embodiments, forming a shell comprises depositing material through electroless deposition.

Methods of making hollow nanoparticles described herein, in some embodiments, further comprise providing an electrolyte having various properties and compositions. In some embodiments, forming the plurality of gas bubbles and forming the shell occurs in the presence of the electrolyte. In some embodiments, the electrolyte exhibits a pH between about 5 and about 8. In some embodiments, the electrolyte exhibits a pH between about 6 and about 7.

In some embodiments, the electrolyte comprises a metal-containing species. In some embodiments, the electrolyte comprises a metal-containing species capable of undergoing deposition through an oxidation-reduction reaction. In some embodiments, the electrolyte comprises a metal-containing species capable of undergoing electroless deposition. In some embodiments, the electrolyte comprises a metal-containing species comprising a metal capable of being reduced by $H_2$. In some embodiments, the electrolyte comprises a metal-containing species comprising a metal capable of being reduced by $NH_3$. In some embodiments, the electrolyte comprises a metal-containing species capable of being reduced by an aqueous reducing agent. In some embodiments, the electrolyte comprises a plurality of metal-containing species having substantially similar reduction potentials. In some embodiments, for example, each of the plurality of metal-containing species is capable of being reduced by the same reducing agent. In some embodiments, the electrolyte comprises a metal-containing species comprising a metal capable of being oxidized by $O_2$. In some embodiments, the electrolyte comprises a metal-containing species capable of being oxidized by an aqueous oxidizing agent. In some embodiments, the metal-containing species comprises one or more of Fe, Co, Ni, Pd, Pt, Cu, Ag, Au, Zn, and Sn. In some embodiments, the metal-containing species comprises Au. In some embodiments, the metal-containing species comprises one or more of titanium (Ti), zirconium (Zr), Fe, Co, Ni, Cu, Zn, and Sn.

In some embodiments, the electrolyte comprises a reducing agent. Any reducing agent not incompatible with the objectives of the present invention may be used. In some embodiments, the reducing agent comprises one or more of phosphites, hypophosphites, hydrazines, borohydrides, cyanoborohydrides, trialkylamines and trialkylphosphines. In some embodiments, the reducing agent comprises one or more of glyoxylic acid, sodium hypophosphite ($Na_2H_2PO_2$), sodium hypophosphite monohydrate ($Na_2H_2PO_2.H_2O$), formaldehyde, sodium borohydride ($NaBH_4$), sodium cyanoborohydride ($NaBH_3(CN)$), hydrazine ($N_2H_4$), hydrazine monohydrate ($N_2H_4.H_2O$), hydrazine-borane, hydroxylamine hydrochloride, formic acid, trimethylamine borane (DMAB), thiourea, ascorbic acid, titanium trichloride, lithium aluminum hydride, triethylsilane, mercaptosuccinic acid, 9-borabicyclo[3.3.1]nonane, gelatin, and sodium citrate. In some embodiments, the electrolyte comprises an oxidizing agent. Any oxidizing agent not incompatible with the objectives of the present invention may be used. In some embodiments, the oxidizing agent comprises one or more of permanganates, chromates, dichromates, perchlorates, and peroxides.

In some embodiments, the electrolyte comprises a stabilizing ligand. In some embodiments, the stabilizing ligand is operable to stabilize one or more hollow nanoparticles against aggregation or agglomeration. In some embodiments, the stabilizing ligand comprises a species having a first end operable to associate with a surface of one or more hollow nanoparticles and a second end operable to interact with solution. In some embodiments, the stabilizing ligand comprises a surfactant. In some embodiments, the stabilizing ligand comprises a thiol. In some embodiments, the stabilizing ligand comprises one or more of an amine, a phosphine, a carboxylic acid, and a carboxylate. Non-limiting examples of stabilizing ligands suitable for use in some embodiments include mercaptoacetic acid, mercaptopropionic acid, hexadecylamine, triphenylphosphine, cetyltrimethylammonium bromide, citric acid and sodium citrate.

In some embodiments, a method of making hollow nanoparticles comprises forming a plurality of gas bubbles, and forming a shell on the surface of at least one of the plurality of gas bubbles to form a hollow nanoparticle, wherein at least one of the gas bubbles is electrochemically generated and wherein forming the plurality of gas bubbles and forming the shell occurs in the presence of an electrolyte, the electrolyte comprising a metal-containing species and one or more promoters. In some embodiments, at least one promoter comprises ethylenediamine (EDA). In some embodiments, at least one promoter comprises ethylenediaminetetraacetic acid (EDTA). In some embodiments, at least one promoter comprises $(SO_3)^{2-}$. In some embodiments, at least one promoter comprises one or more of $Ni^{2+}$, $Pd^{2+}$, and $Pt^{2+}$. In some embodiments, at least one promoter comprises $Ni^{2+}$.

Methods of making hollow nanoparticles described herein, in some embodiments, comprise providing one or more nucleation substrates. In some embodiments, forming a plurality of gas bubbles comprises forming at least one gas bubble on at least one nucleation substrate. In some embodiments, at least one nucleation substrate comprises a solid surface. In some embodiments, at least one nucleation substrate comprises a surface that operates as a working electrode. In some embodiments, the nucleation substrate comprises at least one surface that does not operate as an electrode.

In some embodiments, at least one nucleation substrate comprises an organic polymer. In some embodiments, at least one nucleation substrate comprises an inorganic material. In some embodiments, at least one nucleation substrate comprises a nanoparticle. In some embodiments, at least one nucleation substrate comprises silver (Ag). In some embodiments, at least one nucleation substrate comprises silicon (Si). In some embodiments, at least one nucleation substrate comprises silica ($SiO_2$). In some embodiments, at least one nucleation substrate comprises titania ($TiO_2$). In some embodiments, at least one nucleation substrate comprises alumina ($Al_2O_3$). In some embodiments, at least one nucleation substrate comprises copper (Cu). In some embodiments, at least one nucleation substrate comprises carbon (C). In some embodiments, at least one nucleation substrate comprises a patterned substrate. In some embodiments, at least one nucleation substrate comprises a patterned glass substrate. In some embodiments, at least one nucleation substrate comprises a $SiO_2$ substrate comprising at least one Ag stripe. In some embodiments, at least one nucleation substrate comprises a TEM grid.

In some embodiments, at least one nucleation substrate comprises a membrane. In some embodiments, the membrane has a high surface area. In some embodiments, the membrane comprises a track etched membrane. In some embodiments, the membrane comprises polycarbonate. In some embodiments, the membrane comprises polyester. In some embodiments, the membrane comprises cellulose. In some embodiments, the membrane comprises one or more of regenerated cellulose, cellulose acetate, cellulose nitrate, and mixed cellulose ester. In some embodiments, the membrane comprises polytetrafluoroethylene (PTFE). In some embodiments, the membrane comprises polyamide. In some embodiments, the membrane comprises nylon. In some embodiments, the membrane comprises polyethersulfone (PES). In some embodiments, the membrane comprises polypropylene. In some embodiments, the membrane comprises porous glass. In some embodiments, the membrane comprises anodic aluminum oxide (AAO). In some embodiments, the membrane comprises pores having a diameter of about 100 nm to about 3000 nm. In some embodiments, the membrane comprises pores having a diameter of about 100 nm to about 500 nm.

Methods of making hollow nanoparticles described herein, in some embodiments, comprise providing a plurality of nucleation substrates. In some embodiments, the plurality of nucleation substrates comprises stacked membranes. In some embodiments, the plurality of nucleation substrates comprises stacked membranes comprising anodic aluminum oxide. Methods of making hollow nanoparticles described herein, in some embodiments, further comprise selectively dissolving one or more nucleation substrates following forming a shell.

In some embodiments, a method of making hollow nanoparticles comprises forming a plurality of gas bubbles, forming a shell on the surface of at least one of the plurality of gas bubbles to form a hollow nanoparticle, providing one or more precursors of at least one second nanoparticle, and forming at least one second nanoparticle from the one or more precursors within a cavity defined by the shell, wherein at least one of the gas bubbles is electrochemically generated. In some embodiments, the shell substantially surrounds at least one second nanoparticle. In some embodiments, providing one or more precursors of at least one second nanoparticle comprises providing a first precursor before providing a second precursor. In some embodiments, providing one or more precursors of at least one second nanoparticle comprises providing at least one aqueous solution of the one or more precursors.

In some embodiments, a method of making hollow nanoparticles comprises forming a plurality of gas bubbles, forming a shell on the surface of at least one of the plurality of gas bubbles to form a hollow nanoparticle, providing one or more precursors of a plurality of second nanoparticles, and forming the plurality of second nanoparticles from the one or more precursors within a cavity defined by the shell, wherein at least one of the gas bubbles is electrochemically generated. In some embodiments, the shell substantially surrounds the plurality of second nanoparticles.

Methods of making hollow nanoparticles described herein, in some embodiments, further comprise associating one or more species to one or more outer surfaces of the shell. In some embodiments, one or more species are associated with an outer surface of the shell directly. In some embodiments, one or more species are associated with an outer surface indirectly. In some embodiments, one or more species are associated with an outer surface indirectly through one or more species that are associated with the outer surface directly. In some embodiments, one or more species associated with an outer surface of the shell comprises a polyethylene glycol moiety. In some embodiments, one or more species associated with an outer surface of the shell comprises a targeting agent. In some embodiments, one or more species associated with an outer surface of the shell comprises a Raman active species.

In some embodiments of methods of making hollow nanoparticles described herein, the method is a one-pot method. In some embodiments, a one-pot method comprises forming the nanoparticles from one or more starting materials in one pot or in a single reaction vessel. In some embodiments, none of the starting materials in the single reaction vessel comprises a pre-formed nanoparticle. In some embodiments, none of the starting materials in the single reaction vessel comprises a solid pre-formed nanoparticle. In some embodiments of methods of making hollow nanoparticles described herein, the method is a one-step method. In some embodiments, a one-step method comprises forming the hollow nanoparticles without first making solid cores for the hollow nanoparticles.

In some embodiments, hollow nanoparticles made in accordance with one or more methods described herein can have any of the properties recited herein for hollow nanoparticles. For example, in some embodiments, a method of making hollow nanoparticles described herein comprises making hollow nanoparticles having a cavity having a size or shape as described herein. In some embodiments, a method of making hollow nanoparticles described herein comprises making hollow nanoparticles having a shell having a thickness or composition as described herein.

In another aspect, composite particles are described herein, which, in some embodiments, may offer one or more advantages over prior composite particles. In some embodiments, for example, a composite particle described herein exhibits theranostic and/or dual imaging properties. In some embodiments, a composite particle described herein is useful for magnetic resonance imaging (MRI) and positron emission tomography (PET). In some embodiments, a composite particle described herein is non-toxic. In some embodiments, a composite particle described herein is operable for photothermal therapy.

In some embodiments, a composite particle comprises at least one nanoparticle and a polycrystalline metal shell substantially encapsulating at least one nanoparticle, wherein at least one surface of at least one nanoparticle is not in contact with the shell. In some embodiments, a composite particle comprises at least one nanoparticle and a metal shell substantially encapsulating at least one nanoparticle, wherein the metal shell has a thickness of about 10 nm to about 200 nm and at least one surface of the at least one nanoparticle is not in contact with the shell. In some embodiments, no surface of at least one nanoparticle is in contact with the shell. In some embodiments, no surface of any nanoparticle is in contact with the shell. In some embodiments, the shell is metallic.

In some embodiments, a composite particle comprises a plurality of nanoparticles and a polycrystalline metal shell substantially encapsulating the plurality of nanoparticles, wherein at least one surface of at least one nanoparticle is not in contact with the shell. In some embodiments, a composite particle comprises a plurality of nanoparticles and a metal shell substantially encapsulating the plurality of nanoparticles, wherein the metal shell has a thickness of about 10 nm to about 200 nm and at least one surface of at least one nanoparticle is not in contact with the shell. In some embodiments, no surface of at least one nanoparticle is in contact with the shell. In some embodiments, no surface of any nanoparticle is in contact with the shell. In some embodiments, the shell is metallic.

Composites described herein, in some embodiments, can exhibit various sizes and morphologies. In some embodiments, the composite particle is substantially spherical. In some embodiments, the composite particle is substantially spherical and has a diameter of about 60 nm to about 1000 nm. In some embodiments, the composite particle has a diameter of about 80 nm to about 160 nm, about 100 nm to about 150 nm, about 50 nm to about 100 nm, or about 50 nm to about 160 nm.

Composites described herein, in some embodiments, comprise shells having various thicknesses, morphologies, and compositions. In some embodiments, the shell is porous. In some embodiments, the shell has pores that are smaller than at least one nanoparticle. In some embodiments, the shell has pores ranging in size from about 0.5 nm to about 3 nm. In some embodiments, the shell has pores ranging in size from about 2 nm to about 3 nm. In some embodiments, the shell is non-porous.

In some embodiments, the shell is polycrystalline. In some embodiments, the shell is polycrystalline and has a grain size of about 3 nm to about 8 nm. In some embodiments, the shell is polycrystalline and has a grain size of about 5 nm to about 8 nm. In some embodiments, the shell is polycrystalline and has a grain size less than about 5 nm. In some embodiments, the shell is single crystalline.

In some embodiments, the shell has a thickness of about 10 nm to about 100 nm. In some embodiments, the shell has a thickness greater than about 20 nm. In some embodiments, the shell has a thickness between about 10 nm and about 20 nm. In some embodiments, the shell has a thickness of about 10 nm to about 45 nm, about 25 nm to about 45 nm, or about 45 nm to about 200 nm.

In some embodiments, the shell has a surface roughness of less than about 5 nm. In some embodiments, the shell has a surface roughness between about 5 nm and 8 nm. In some embodiments, the shell has a surface roughness between about 3 nm and about 8 nm. In some embodiments, the shell has a surface roughness less than about 3 nm. In some embodiments, the shell has a surface roughness greater than about 8 nm.

In some embodiments, the shell comprises one or more of Fe, Co, Ni, Pd, Pt, Cu, Ag, Au, Zn, and Sn. In some embodiments, the shell comprises Au.

Composite particles described herein, in some embodiments, exhibit various optical properties. In some embodiments, a composite particle described herein exhibits an absorption profile comprising a surface plasmon resonance peak. In some embodiments, the composite particle exhibits a surface plasmon resonance peak between about 600 nm and about 900 nm. In some embodiments, the composite particle exhibits a surface plasmon resonance peak between about 600 nm and about 750 nm. In some embodiments, the composite particle exhibits a surface plasmon resonance peak between about 650 nm and about 900 nm. In some embodiments, the composite particle exhibits a surface plasmon resonance peak between about 700 nm and about 800 nm.

Composite particles described herein, in some embodiments, comprise nanoparticles having various sizes, morphologies, compositions, and properties. In some embodiments, at least one nanoparticle is substantially spherical. In some embodiments, at least one nanoparticle is substantially spherical and has a diameter of less than about 50 nm. In some embodiments, at least one nanoparticle has a diameter of less than about 20 nm. In some embodiments, at least one nanoparticle has a diameter between about 5 nm and about 20 nm. In some embodiments, at least one nanoparticle has a diameter between about 30 nm and about 50 nm. In some embodiments, at least one nanoparticle comprises a cluster of nanoparticles.

In some embodiments, at least one nanoparticle comprises a magnetic nanoparticle. In some embodiments, the magnetic nanoparticle is superparamagnetic. In some embodiments, the magnetic nanoparticle is ferromagnetic. In some embodiments, at least one nanoparticle comprises iron oxide. In some embodiments, the nanoparticle comprises doped $Fe_3O_4$. In some embodiments, doped $Fe_3O_4$ comprises one or more nuclides useful for positron emission tomography (PET). In some embodiments, doped $Fe_3O_4$ comprises one or more of $^{64}Cu$, $^{89}Zr$, $^{11}C$, $^{18}F$, and $^{67}Ga$. In some embodiments, doped $Fe_3O_4$ comprises one or more of $^{64}Cu$ and $^{89}Zr$.

In some embodiments, at least one nanoparticle comprises an organic nanoparticle. In some embodiments, at least one nanoparticle comprises an inorganic nanoparticle. In some embodiments, at least one nanoparticle comprises a semiconductor nanoparticle. In some embodiments, at least one nanoparticle comprises a metal nanoparticle. In some embodiments, at least one nanoparticle comprises a metal oxide nanoparticle. In some embodiments, at least one nanoparticle comprises a ceramic nanoparticle. In some embodiments, at least one nanoparticle comprises a quantum dot.

Composite particles described herein, in some embodiments, further comprise various species associated with an outer surface of the composite particle. In some embodiments, one or more species are associated with an outer surface directly. In some embodiments, one or more species are associated with an outer surface indirectly. In some embodiments, one or more species are associated with an outer surface indirectly through one or more species that are associated with the outer surface directly. In some embodiments, at least one species associated with an outer surface comprises a Raman active species. In some embodiments, at least one species associated with an outer surface comprises a polyethylene glycol moiety. In some embodiments, at least one species associated with an outer surface comprises a targeting agent. In some embodiments, a first species associated with an outer surface comprises a Raman active species and forms a first layer and a second species associated with the outer surface comprises a polyethylene glycol moiety and forms a second layer, wherein the second layer substantially surrounds the first layer. In some embodiments, a first species associated with an outer surface comprises a polyethylene glycol moiety and a second species associated with the outer surface comprises a targeting agent.

In another aspect, methods of making a composite particle are described herein, which, in some embodiments, may offer one or more advantages over prior methods of making a composite particle. In some embodiments, for example, a method of making a composite particle described herein is simple, efficient, scalable, inexpensive, and reproducible. In some embodiments, a method of making a composite particle comprises providing a porous hollow nanoparticle, providing one or more precursors of at least one second nanoparticle, mixing the one or more precursors with the hollow nanoparticle, and forming at least one second nanoparticle from the one or more precursors within the hollow nanoparticle. In some embodiments, a method of making a composite particle comprises providing a porous hollow nanoparticle, providing one or more precursors of a plurality of second nanoparticles, mixing the one or more precursors with the hollow nanoparticle, and forming the plurality of second nanoparticles from the one or more precursors within the hollow nanoparticle. In some embodiments, the hollow nanoparticle comprises any porous hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making composite particles described herein, in some embodiments, comprise providing and mixing one or more precursors of at least one second nanoparticle in various forms and ways. In some embodiments, providing one or more precursors of at least one second nanoparticle comprises providing at least one aqueous solution of the one or more precursors. In some embodiments, mixing one or more precursors of at least one second nanoparticle comprises mixing a first precursor with the hollow nanoparticle before mixing a second precursor with the hollow nanoparticle. In some embodiments, mixing the one or more precursors of at least one second nanoparticle with the hollow nanoparticle comprises immersing the hollow nanoparticle in the at least one aqueous solution. In some embodiments, mixing the one or more precursors of at least one second nanoparticle with the hollow nanoparticle comprises flowing one or more aqueous solutions of one or more precursors of the at least one second nanoparticle through a membrane comprising the hollow nanoparticle. In some embodiments, flowing one or more aqueous solutions through a membrane comprises flowing one or more aqueous solutions through a membrane using vacuum filtration.

Methods of making composite particles described herein, in some embodiments, further comprise sealing the porous hollow nanoparticle. In some embodiments, sealing comprises providing a metal-containing species capable of undergoing deposition by an oxidation-reduction reaction on the surface of the porous hollow nanoparticle. In some embodiments, sealing comprises providing a metal-containing species capable of undergoing electroless deposition on the surface of the porous hollow nanoparticle.

Methods of making composite particles described herein, in some embodiments, further comprise associating one or more species to an outer surface of the composite particle. In some embodiments, one or more species are associated with an outer surface directly. In some embodiments, one or more species are associated with an outer surface indirectly. In some embodiments, one or more species are associated with an outer surface indirectly through one or more species that are associated with the outer surface directly. In some embodiments, one or more species associated with an outer surface comprises a polyethylene glycol moiety. In some embodiments, one or more species associated with an outer surface comprises a targeting agent. In some embodiments, one or more species associated with an outer surface comprises a Raman active species.

In some embodiments, a method of making a composite particle comprises providing a porous hollow nanoparticle, providing one or more therapeutic agents, and mixing the one or more therapeutic agents with the hollow nanoparticle to dispose at least one of the therapeutic agents within the hollow nanoparticle. In some embodiments, the hollow nanoparticle comprises any porous hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making a composite particle described herein, in some embodiments, comprise providing and mixing one or more therapeutic agents in various forms and ways. In some embodiments, providing one or more therapeutic agents comprises providing at least one aqueous solution of the one or more therapeutic agents. In some embodiments, mixing the one or more therapeutic agents with the hollow nanoparticle comprises immersing the hollow nanoparticle in at least one aqueous solution. In some embodiments, mixing the one or more therapeutic agents with the hollow nanoparticle comprises flowing one or more aqueous solutions of one or more therapeutic agents through a membrane comprising the hollow nanoparticle. In some embodiments, flowing one or more aqueous solutions through a membrane comprises flowing one or more aqueous solutions through a membrane using vacuum filtration. In some embodiments, mixing the one or more therapeutic agents with the hollow nanoparticle comprises mixing at a temperature higher than about 25° C. In some embodiments, mixing the one or more therapeutic agents with the hollow nanoparticle comprises mixing at a temperature higher than about 37° C. In some embodiments, mixing the one or more therapeutic agents with the hollow nanoparticle comprises mixing at a temperature higher than about 40° C., higher than about 50° C., higher than about 60° C., higher than about 70° C., higher than about 80° C., or higher than about 90° C.

In some embodiments, a method of making a composite particle comprises providing a porous hollow nanoparticle, providing one or more therapeutic agents, mixing the one or more therapeutic agents with the hollow nanoparticle to dispose at least one of the therapeutic agents within the hollow nanoparticle, and sealing the porous hollow nanoparticle. In some embodiments, sealing comprises providing a metal-containing species capable of undergoing deposition through an oxidation-reduction reaction on the surface of the porous hollow nanoparticle. In some embodiments, sealing comprises providing a metal-containing species capable of undergoing electroless deposition on the surface of the porous hollow nanoparticle.

In some embodiments, a method of making a composite particle comprises providing a porous hollow nanoparticle, providing one or more therapeutic agents, mixing the one or more therapeutic agents with the hollow nanoparticle to dispose at least one of the therapeutic agents within the hollow nanoparticle, and associating one or more species with an outer surface of the composite particle. In some embodiments, at least one species associated with an outer surface comprises a polyethylene glycol moiety. In some embodiments, at least one species associated with an outer surface comprises a targeting agent. In some embodiments, at least one species associated with an outer surface comprises a Raman active species.

In some embodiments, a method of making a composite particle comprises providing a hollow nanoparticle, providing one or more Raman active species, and mixing the one or more active Raman species with the hollow nanoparticle to associate at least one of the Raman active species with an outer surface of the hollow nanoparticle. In some embodiments, the hollow nanoparticle comprises any hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making a composite particle described herein, in some embodiments, comprise providing and mixing one or more Raman active species in various forms and ways. In some embodiments, providing one or more Raman active species comprises providing at least one aqueous solution of the one or more Raman active species. In some embodiments, at least one aqueous solution comprises at least one Raman active species in a concentration greater than or equal to about 1 µM. In some embodiments, at least one aqueous solution comprises at least one Raman active species in a concentration greater than or equal to about 10 µM, greater than or equal to about 100 µM, or greater than or equal to about 1000 µM. In some embodiments, at least one aqueous solution comprises at least one Raman active species in a concentration between about 1 µM and about 1 mM. In some embodiments, at least one aqueous solution comprises at least one Raman active species in a concentration between about 30 µM and about 50 µM. In some embodiments, mixing the one or more Raman active species with the hollow nanoparticle comprises immersing the hollow nanoparticle in at least one aqueous solution comprising at least one Raman active species. In some embodiments, mixing the one or more Raman active species with the hollow nanoparticle comprises immersing a membrane comprising the hollow nanoparticle in at least one aqueous solution comprising at least one Raman active species. In some embodiments, mixing the one or more Raman active species with the hollow nanoparticle comprises flowing at least one solution comprising at least one Raman active species through a membrane comprising the hollow nanoparticle. In some embodiments, flowing one or more aqueous solutions through a membrane comprises flowing one or more aqueous solutions through a membrane using vacuum filtration.

In some embodiments, a method of making a composite particle comprises providing a hollow nanoparticle, providing one or more Raman active species, mixing the one or more active Raman species with the hollow nanoparticle to associate at least one of the Raman active species to an outer surface of the hollow nanoparticle, providing one or more species comprising a polyethylene glycol moiety, and mixing the one or more species comprising a polyethylene glycol moiety to associate at least one species comprising a polyethylene glycol moiety to an outer surface of the hollow nanoparticle. In some embodiments, association with an outer surface of the hollow nanoparticle is direct association. In some embodiments, association with an outer surface of the hollow nanoparticle is indirect association. In some embodiments, the Raman active species forms a first layer and the species comprising a polyethylene glycol moiety forms a second layer, wherein the second layer substantially surrounds the first layer. In some embodiments, the method is a one-pot method. In some embodiments, the method is a one-step method.

In some embodiments, composite particles made in accordance with one or more methods described herein can have any of the properties recited herein for composite particles or hollow nanoparticles. For example, in some embodiments, a method of making a composite particle described herein comprises making a composite particle having a cavity having a size or shape as described herein. In some embodiments, a method of making a composite particle described herein comprises making a composite particle having a shell having a thickness or composition as described herein. In some embodiments, a method of making a composite particle described herein comprises making a composite particle having one or more species associated with an outer surface as described herein.

In another aspect, methods of imaging and treating biological environments are disclosed herein. A method of imaging a biological environment described herein, in some embodiments, comprises providing a hollow nanoparticle described herein and irradiating the hollow nanoparticle with electromagnetic radiation. A method of treating a biological environment described herein, in some embodiments, comprises providing a hollow nanoparticle described herein and irradiating the hollow nanoparticle with electromagnetic radiation. In some embodiments, both imaging and treating a biological environment can be carried out at substantially the same time. In some embodiments, at least a portion of the electromagnetic radiation is inelastically scattered by the hollow nanoparticle. In some embodiments, at least a portion of the electromagnetic radiation interacts with a surface plasmon of the hollow nanoparticle. In some embodiments, irradiating induces photothermal heating. In some embodiments, irradiating induces rupturing of the hollow nanoparticle. In some embodiments, imaging a biological environment comprises imaging with surface plasmon resonance (SPR) imaging. In some embodiments, imaging a biological environment comprises imaging with surface enhanced Raman spectroscopy (SERS). In some embodiments, imaging a biological environment comprises imaging with magnetic resonance imaging (MRI). In some embodiments, imaging a biological environment comprises imaging with positron emission tomography (PET). In some embodiments, imaging a biological environment comprises imaging with a combination of two or more of SPR imaging, SERS, MRI, and PET. In some embodiments, treating a biological environment comprises treating cancer.

In another aspect, methods of delivering a payload are described herein, which, in some embodiments, may offer one or more advantages over prior methods of delivering a payload. In some embodiments, for example, a method of delivering a payload described herein is safe and efficient. In some embodiments, a method of delivering a payload comprises providing a hollow nanoparticle comprising a shell, a cavity substantially defined by the shell, and a payload within the cavity; and releasing the payload. In some embodiments, the hollow nanoparticle comprises any hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of delivering a payload described herein, in some embodiments, comprise releasing the payload in various ways. In some embodiments, releasing comprises rupturing the shell. In some embodiments, rupturing the shell comprises directing radiation onto the nanoparticle. In some embodiments, directing radiation comprises directing visible radiation. In some embodiments, directing radiation comprises directing near infrared (NIR) radiation. In some embodiments, releasing the payload comprises allowing the payload to diffuse out of the nanoparticle. In some embodiments, the payload comprises a gas. In some embodiments, the gas comprises $H_2$. In some embodiments, the payload comprises a therapeutic agent. In some embodiments, the payload comprises a gene.

In some embodiments of methods of delivering a payload described herein, the payload is provided within the cavity by immersing the hollow nanoparticle in a solution comprising the payload. In some embodiments, the payload is provided within the cavity by immersing a membrane comprising the hollow nanoparticle in a solution comprising the payload. In some embodiments, the payload is provided within the cavity by flowing one or more solutions comprising the payload through a membrane comprising the hollow nanoparticle. In some embodiments, the payload is provided by mixing the hollow nanoparticle with the payload under high pressure, wherein the hollow nanoparticle has a porous shell. In some embodiments, the payload is provided within the cavity at an elevated temperature. In some embodiments, the payload is provided within the cavity at a temperature higher than about 25° C., higher than about 37° C., higher than about 40° C., higher than about 50° C., higher than about 60° C., higher than about 70° C., higher than about 80° C., or higher than about 90° C.

Methods of delivering a payload described herein, in some embodiments, comprise providing any hollow nanoparticle or composite particle described herein.

In another aspect, methods of selectively depositing hollow nanoparticles on a surface are described herein, which, in some embodiments, may offer one or more advantages over prior methods. In some embodiments, for example, a method of selectively depositing hollow nanoparticles on a surface described herein is simple and efficient. In some embodiments, a method of selectively depositing hollow nanoparticles on a surface comprises providing a substrate having a plurality of domains with differing hydrophobicity, forming a plurality of gas bubbles, and forming a shell on the surface of at least one of the plurality of gas bubbles to form a hollow nanoparticle. In some embodiments, the hollow nanoparticles are selectively deposited on one or more domains having a first hydrophobicity. In some embodiments, the substrate comprises a patterned substrate.

Methods of selectively depositing hollow nanoparticles on a surface described herein, in some embodiments, comprise depositing any hollow nanoparticles described herein.

Some embodiments described herein comprise nanoparticles having cavities of various sizes. In some embodiments, cavity size can be varied by altering one or more of a number of synthetic parameters, including electrolyte composition and pH, applied potential, applied potential time profile, and nucleation substrate composition. Not intending to be bound by theory, it is believed that cavity size is affected by the size of corresponding gas bubbles. In some embodiments, the size of gas bubbles described herein can be varied by altering one or more synthetic parameters, including electrolyte composition, stability, and pH; applied potential; applied potential time profile; working electrode composition; and the hydrophobicity and surface morphology of the nucleation substrate. Again not intending to be bound by theory, it is believed that the size and size distribution of gas bubbles described herein is affected by the efficiency and extent of electrochemical gas generation. In some embodiments, altering one or more of the foregoing synthetic parameters alters the efficiency of electrochemical gas generation. In some embodiments, altering one or more of the foregoing synthetic parameters alters the exchange current density.

Some embodiments described herein comprise hollow nanoparticles and composite particles having various sizes. In some embodiments, hollow nanoparticle or composite particle size can be varied by altering one or more of a number of synthetic parameters, including electrolyte composition and pH, applied potential, applied potential time profile, nucleation substrate composition, and reaction time. Not intending to be bound by theory, it is believed that hollow nanoparticle or composite particle size is affected by the size of corresponding gas bubbles. Therefore, in some embodiments, hollow nanoparticle or composite particle size can be controlled by altering synthetic parameters affecting the nucleation of gas bubbles on a substrate. In some embodiments, hollow nanoparticle or composite particle size is affected by shell thickness. Therefore, in some embodiments, hollow nanoparticle or composite particle size can be controlled by altering the shell thickness.

Some embodiments described herein comprise shells having various thicknesses. In some embodiments, shell thickness can be varied by altering a number of synthetic parameters, including electrolyte composition and pH, applied potential, applied potential time profile, and reaction time.

Some embodiments described herein comprise hollow nanoparticles or composite particles exhibiting various surface plasmon resonance peaks. In some embodiments, SPR peak wavelength can be varied by altering one or more of a number of parameters, including hollow nanoparticle or composite particle composition, surface roughness, and shell thickness.

Some embodiments described herein comprise shells, hollow nanoparticles, or composite particles having various surface roughnesses. In some embodiments, surface roughness can be varied by altering one or more of electrolyte composition and pH, reaction time, applied potential, and applied potential time profile.

Some embodiments described herein comprise shells having various compositions. In some embodiments, shell composition can be varied by altering the electrolyte composition. In some embodiments, the electrolyte composition can be altered by changing the identity of one or more metal-containing species. Not intending to be bound by theory, in some embodiments, shells having various compositions can be provided by using electrolytes comprising one or more metal-containing species, wherein at least one metal-containing species can be reduced or oxidized by at least one electrochemically generated gas. Again not intending to be bound by theory, in some embodiments, shells having various compositions can be provided by using electrolytes comprising one or more metal-containing species, wherein at least one metal-containing species is operable to undergo deposition through an oxidation-reduction reaction. In some embodiments, at least one metal-containing species is operable to undergo electroless deposition. In some embodiments, a plurality of metal-containing species have substantially similar reduction potentials. In some embodiments, shells having various compositions can be provided by using electrolytes comprising one or more metal-containing species, wherein at least one metal-containing species is operable to undergo deposition through an oxidation-reduction reaction on the surface of a gas bubble. In some embodiments, shells having various compositions can be provided by using electrolytes comprising one or more metal-containing species, wherein at least one metal-containing species is operable to undergo electroless deposition on the surface of a gas bubble. In some embodiments, shells having various compositions can be provided by using electrolytes comprising one or more metal-containing species, wherein at least one metal-containing species is operable to undergo deposition through oxidation-reduction on the surface of a metal shell. In some embodiments, shells having various compositions can be provided by using electrolytes comprising one or more metal-containing species, wherein at least one metal-containing species is operable to undergo electroless deposition on the surface of a metal shell.

Some embodiments described herein comprise pores of various sizes. In some embodiments, pore size can be controlled by altering one or more of reaction time, electrolyte composition and pH, applied potential, and applied potential time profile. In some embodiments, altering the electrolyte composition comprises altering the concentration of a metal-containing species in the electrolyte. In some embodiments, altering the electrolyte composition comprises altering the concentration of a reducing agent in the electrolyte.

Some embodiments described herein comprise forming at least one second nanoparticle within a porous shell, wherein the at least one second nanoparticle has various sizes. In some embodiments, the size of the at least one second nanoparticle can be controlled by altering one or more of the reaction time, the concentration of one or more precursors of the at least one second nanoparticle, the pore size, and the cavity size.

Some embodiments described herein comprise a therapeutic agent. Any suitable therapeutic agent not incompatible with the objectives of the present invention may be used. In some embodiments, the therapeutic agent comprises a gas. In some embodiments, the therapeutic agent comprises a liquid. In some embodiments, the therapeutic agent comprises a solution. In some embodiments, the therapeutic agent comprises a drug. In some embodiments, the therapeutic agent comprises a water-soluble drug. Non-limiting examples of therapeutic agents useful in some embodiments include mitoxantrone and gemcitabine. Suitable therapeutic agents may be purchased from commercial sources or prepared according to methods known in the art.

Some embodiments described herein comprise a targeting agent. Any suitable targeting agent not incompatible with the objectives of the present invention may be used. In some embodiments, the targeting agent comprises a species operable to selectively interact with an analyte. In some embodiments, the targeting agent comprises a species operable to selectively interact with an antigen. In some embodiments, the targeting agent comprises one or more of proteins, antibodies, peptides, and small molecules. In some embodiments, the targeting agent comprises a protein. In some embodiments, the targeting agent comprises an antibody. In some embodiments, the targeting agent comprises a peptide. In some embodiments, the targeting agent comprises a small molecule. Non-limiting examples of targeting agents useful in some embodiments include streptavidin, biotin, anti-PSMA, $NH_2GR_{11}$, and c(RGDyK). Suitable species may be purchased from commercial sources or prepared according to methods known in the art.

Some embodiments described herein comprise a Raman active species. Any suitable Raman active species not incompatible with the objectives of the present invention may be used. In some embodiments, the Raman active species comprises a positive charge. In some embodiments, the Raman active species comprises a delocalized $\pi$ system. In some embodiments, the Raman active species comprises a thiol moiety. In some embodiments, the Raman active species comprises a thiol moiety operative to form a sulfur-metal bond with a surface. Non-limiting examples of Raman active species useful in some embodiments include cresyl violet, nile blue, rhodamine 6G, tetrafluoroborate, diethylthiatricarbocyanine (DTTC), DTTC iodide, crystal violet, IR140 (meso-diphenylamine substituted heptamethine), HITC iodide (1,1',3,3,3',3'-hexamethylindotrycarbocyanine iodide), and DOTC iodide (3-ethyl-2-[7-(3-ethyl-2(3H)-benzoxazolylidene)-1,3,5-heptatrienyl]-benzoxazolium iodide). Suitable species may be purchased from commercial sources or prepared according to methods known in the art. In some embodiments comprising a Raman active species, the dynamic range of hollow nanoparticle detection is up to about 30 dB. In some embodiments, the dynamic range of hollow nanoparticle detection is about 10 µM to about 10 nM.

Some embodiments described herein comprise a species comprising a polyethylene glycol (PEG) moiety. Any suitable species comprising a polyethylene glycol moiety not incompatible with the objectives of the present invention may be used. In some embodiments, a species comprises a monofunctional methyl ether PEG (mPEG) moiety. In some embodiments, a species comprises a thiolated polyethylene glycol moiety. In some embodiments, a species comprises a polyethylene glycol moiety and a carboxylic acid moiety. In some embodiments, a species comprises a thiolated polyethylene glycol moiety and a carboxylic acid moiety. In some embodiments, a species comprises an oligomeric or polymeric species comprising a polyethylene glycol moiety and having two ends, wherein one end comprises a thiol moiety and the other end comprises a carboxylic acid moiety. In some embodiments, a species has the formula $HS-(OCH_2CH_2)_n-COOH$. Suitable species may be purchased from commercial sources or prepared according to methods known in the art.

Some embodiments described herein comprise associating one or more species with an outer surface. Any suitable method of associating not incompatible with the objectives of the present invention may be used. In some embodiments, associating comprises forming one or more covalent bonds between an outer surface and one or more species associated with the outer surface. In some embodiments, associating comprises forming one or more metal-sulfur bonds. In some embodiments, associating comprises forming one or more Au—S bonds. In some embodiments, associating comprises forming one or more non-covalent bonds between an outer surface and one or more species associated with the outer surface. In some embodiments, forming one or more non-covalent bonds comprises forming one or more hydrogen bonds. In some embodiments, associating comprises forming one or more ionic bonds. In some embodiments, associating comprises forming one or more electrostatic interactions between an outer surface and one or more species associated with the outer surface. In some embodiments, associating comprises forming one or more hydrophobic interactions between an outer surface and one or more species associated with the outer surface. In some embodiments, associating comprises forming one or more van der Waals interactions.

In some embodiments, associating comprises forming one or more direct associations (such as covalent bonds, non-covalent bonds, hydrogen bonds, ionic bonds, electrostatic interactions, or van der Waals interactions) between an outer surface and one or more first species directly associated with the outer surface and further forming one or more associations between at least one first species and at least one second species not directly associated with the outer surface. In some embodiments, the first species and the second species are associated by one or more covalent bonds, non-covalent bonds, hydrogen bonds, ionic bonds, electrostatic interactions, or van der Waals interactions. In some embodiments, the first species and the second species are associated through covalent coupling chemistry. In some embodiments, the first species and the second species are associated through carbodiimide chemistry. In some embodiments, the first species and the second species are associated through click chemistry. In some embodiments, the first species forms a first layer substantially surrounding the outer surface and the second species forms a second layer substantially surrounding the first layer.

Some embodiments described herein comprise electrochemically generated gas bubbles. In some embodiments, an electrochemically generated gas bubble comprises a gas bubble comprising one or more species formed at the surface of an electrode. In some embodiments, an electrochemically generated gas bubble comprises a gas bubble comprising one or more species formed from an oxidation or reduction reaction occurring at the surface of an electrode.

Some embodiments described herein comprise an electrolyte. Any suitable electrolyte not incompatible with the objectives of the present invention may be used. In some embodiments, the electrolyte comprises an electrolyte operable for the electrodeposition of one or more metals. In some embodiments, the electrolyte comprises an electrolyte operable for the deposition of one or more metals through one or more oxidation-reduction reactions. In some embodiments, the electrolyte comprises an electrolyte operable for the electroless deposition of one or more metals. In some embodiments, the electrolyte comprises a commercial electrolyte. In some embodiments, the electrolyte comprises a modified commercial electrolyte.

Some embodiments described herein comprise an electrolyte comprising a promoter. In some embodiments, a promoter is operable to promote the efficient generation of gas bubbles. In some embodiments, a promoter is operable to promote efficient electrochemical generation of a gas. In some embodiments, a promoter is operable to promote efficient electrochemical generation of hydrogen. In some embodiments, a promoter is operable to promote nucleation of substantially spherical gas bubbles. In some embodiments, a promoter is operable to alter the hydrophobicity of a nucleation substrate. In some embodiments, a promoter is operable to decrease the hydrophobicity of a nucleation substrate. In some embodiments, a promoter is operable to increase the hydrophobicity of a nucleation substrate. In some embodiments, a promoter is operable to increase the hydrophobicity of a substrate comprising alumina. In some embodiments, a promoter is operable to stabilize a metal-containing species. In some embodiments, a promoter is operable to suppress disproportionation of a metal-containing species. In some embodiments, a promoter is operable to remove contaminants from an electrode surface. In some embodiments, a promoter is operable to remove oxide from an electrode surface. In some embodiments, a promoter is operable to undergo electrodeposition onto an electrode surface. In some embodiments, a promoter is operable to increase the exchange current density of the electrode. In some embodiments, a promoter is operable to increase the hydrogen exchange current density of the electrode. In some embodiments, a promoter is operable to increase the current density of gas evolution by about 50% to about 400%. In some embodiments, a promoter is operable to increase the current density of gas evolution by about 100% to about 300%. In some embodiments, a promoter comprises at least one lone pair of electrons capable of binding to a metal. In some embodiments, a promoter comprises at least one lone pair of electrons capable of binding to oxygen. In some embodiments, a promoter comprises a polydentate species. In some embodiments, a promoter comprises a bidentate species. In some embodiments, a promoter comprises a source of one or more solution phase ions that is the same as one or more ions contained in a metal-containing species.

Some embodiments described herein comprise a nucleation substrate. Any suitable nucleation substrate not incompatible with the objectives of the present invention may be used. In some embodiments, a nucleation substrate comprises a surface operable to support the nucleation of one or more gas bubbles. In some embodiments, a nucleation substrate comprises a surface operable to support the nucleation and growth of one or more nanoparticles. In some embodiments, a nucleation substrate comprises a plurality of channels. In some embodiments, a nucleation substrate comprises at least one crack, hole, ridge, or defect. In some embodiments, a nucleation substrate comprises a rough surface. In some embodiments, a nucleation substrate comprises a plurality of domains. In some embodiments, the domains are separated by boundaries or junctions. In some embodiments, one or more domains exhibit different properties. In some embodiments, one or more domains exhibit differing hydrophobicity. In some embodiments, one or more domains exhibit different surface treatment. In some embodiments, a nucleation substrate comprises Ag. In some embodiments, a nucleation substrate comprises Si. In some embodiments, a nucleation substrate comprises $SiO_2$. In some embodiments, a nucleation substrate comprises $TiO_2$. In some embodiments, a nucleation substrate comprises $Al_2O_3$. In some embodiments, a nucleation substrate comprises Cu. In some embodiments, a nucleation substrate comprises C. In some embodiments, a nucleation substrate comprises a patterned substrate. In some embodiments, a nucleation substrate comprises a patterned glass substrate. In some embodiments, a nucleation substrate comprises a $SiO_2$ substrate comprising at least one Ag stripe. In some embodiments, a nucleation substrate operates as a working electrode. In some embodiments, a nucleation substrate comprises a membrane. In some embodiments, the membrane comprises anodic aluminum oxide.

Some embodiments described herein are further illustrated in the following non-limiting examples.

Example 1

Hollow Au Nanoparticles Formed Using Stacked Membranes

Figure 2:
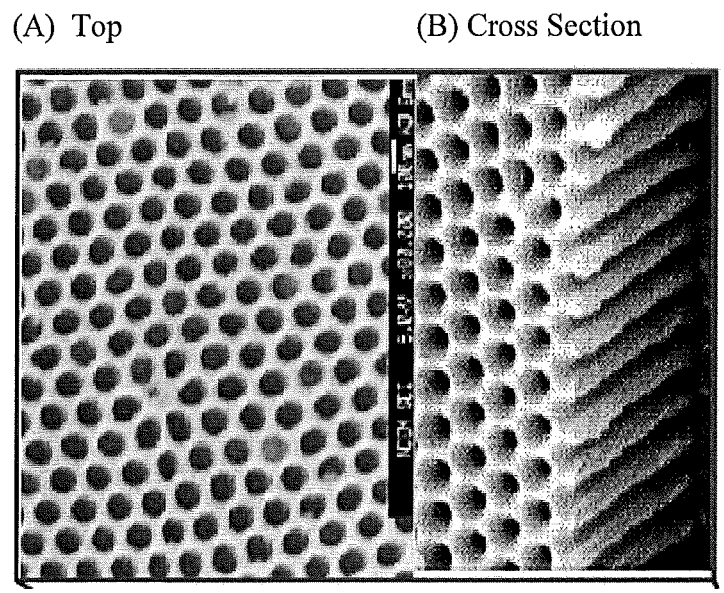
FIG. 2A is a scanning electron microscopy (SEM) image showing a top view of an alumina membrane suitable for use in some methods described herein.
FIG. 2B is an SEM image showing a cross section of an alumina membrane suitable for use in some methods described herein.

Hollow Au nanoparticles consistent with some embodiments herein were provided as follows. The nanoparticles were formed using a three-electrode electrodeposition cell with a Ag/AgCl electrode in 3 M NaCl solution as the reference and a platinum mesh as the counter electrode, as illustrated in FIG. 1. Potentials were applied to the working electrode using a Princeton Applied Research 273A Potentiostat/Galvanostat. A stack of two to five commercial alumina membranes (Whatman Corp.) provided a plurality of nucleation substrates. Each membrane was about 60 μm thick, with channels extending through the entire thickness. One side of each membrane further exhibited small branches. The channel diameter was about 300 nm and the diameter of the branches varied from about 20 nm to about 200 nm. The channel density was approximately $10^9/cm^2$. Top and cross section views of a membrane are shown in FIG. 2. The membranes were stacked such that the branched side of each membrane was closest to the membrane beneath rather than the membrane above, if any (i.e., the branched sides were oriented to be on bottom rather than on top of each layer in the stack of membranes). A 500 nm Cu layer was sputter-deposited on the bottom side of the bottom membrane in the stack and served as the working electrode. A Teflon cell with an o-ring 1 cm in diameter was placed on the top of the membrane stack.

An electrolyte was disposed in the electrodeposition cell described above. The electrolyte was prepared by first preparing an aqueous solution composed of ~3% (by volume) sulfuric acid (18 M, Alfa Aesar), ~3% (by volume) ethylenediamine (EDA, 50% solution diluted from 99%, Sigma-Aldrich), ~10% (by volume) sodium gold sulfite ($Na_3Au(SO_3)_2$, 10% solution diluted from pH 10.5 solution purchased from Colonial Metals, Inc.), and ~7% (by volume) sodium sulfite ($Na_2SO_3$) (2M aqueous solution, Sigma-Aldrich). The solution had a pH of about 7.0. The solution was then altered by adding 0.01 M sulfuric acid ($H_2SO_4$) or 0.4 M aqueous nickel sulfamate ($Ni(SO_3NH_2)_2$, prepared using deionized water and 98% nickel sulfamate tetrahydrate ($Ni(SO_3NH_2)_2 \cdot 4H_2O$) purchased from Sigma-Aldrich) to reduce the pH to ~6.0.

Figure 3:
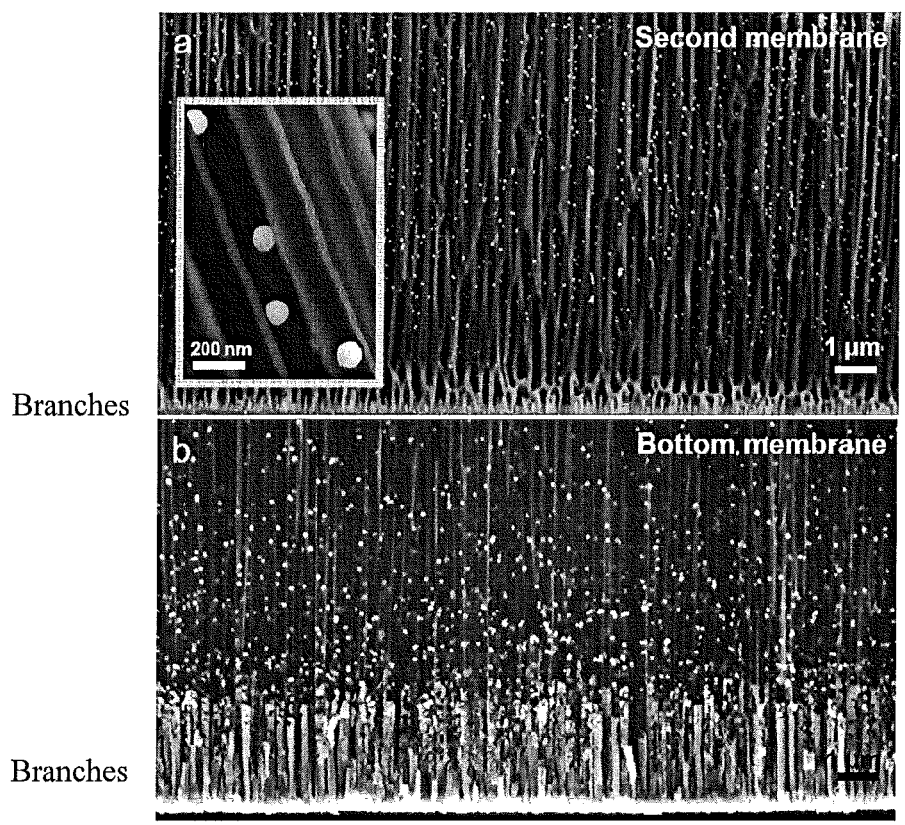
FIG. 3A is an SEM image of an alumina membrane suitable for use in some methods described herein. Scale bar=1 μm. Inset is an enlarged view. Inset scale bar=200 nm.
FIG. 3B is an SEM image of an alumina membrane suitable for use in some methods described herein. Scale bar=1 μm.

After disposing the electrolyte in the electrodeposition cell, a potential more negative than −0.6 V (vs. Ag/AgCl) was applied, resulting in the formation of large Au nanorods and smaller hollow Au nanoparticles. The hollow Au nanoparticles were observed on the inner pore wall surfaces of all the membranes. More hollow nanoparticles were observed in membranes closer to the bottom electrode. The number of these hollow nanoparticles gradually decreased with the distance from the bottom electrode, as shown in FIG. 3. Some electrodeposited Au nanorods can be seen at the bottom of FIG. 4, while some hollow Au nanoparticles can be seen in FIGS. 3 and 4. Branches at the bottom of each membrane can be seen at the bottom of FIG. 3A and FIG. 3B.

Figure 4:
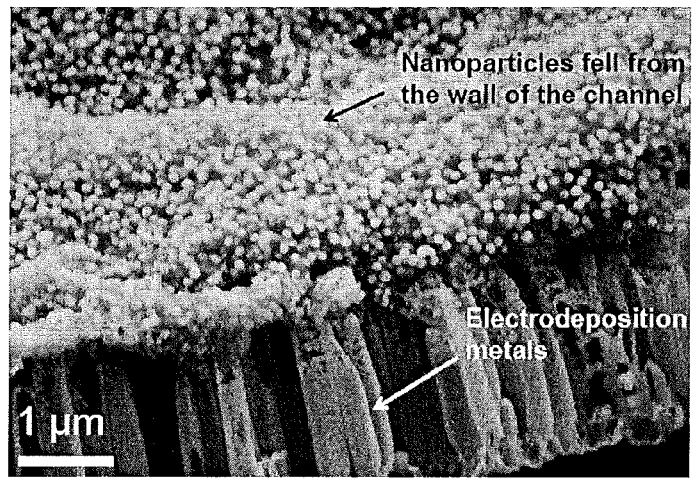
FIG. 4 is an SEM image of hollow gold (Au) nanoparticles according to some embodiments described herein, on electrodeposited metal. Scale bar=1 μm.

The hollow Au nanoparticles were isolated by first pouring out the electrolyte from the cell and washing using deionized water. Deionized water was then added to the cell and kept there for at least half an hour to allow complete diffusion of the electrolyte out of the membranes. This process was repeated at least three times. Membranes in the stack were then individually dissolved using 1 M sodium hydroxide (NaOH) solution. The remaining hollow Au nanoparticles were purified by several cycles of dispersion in deionized water followed by centrifugation. FIG. 4 shows the accumulation of hollow Au nanoparticles on top of the electrodeposited metal on the working electrode after dissolving the first membrane.

Figure 5:
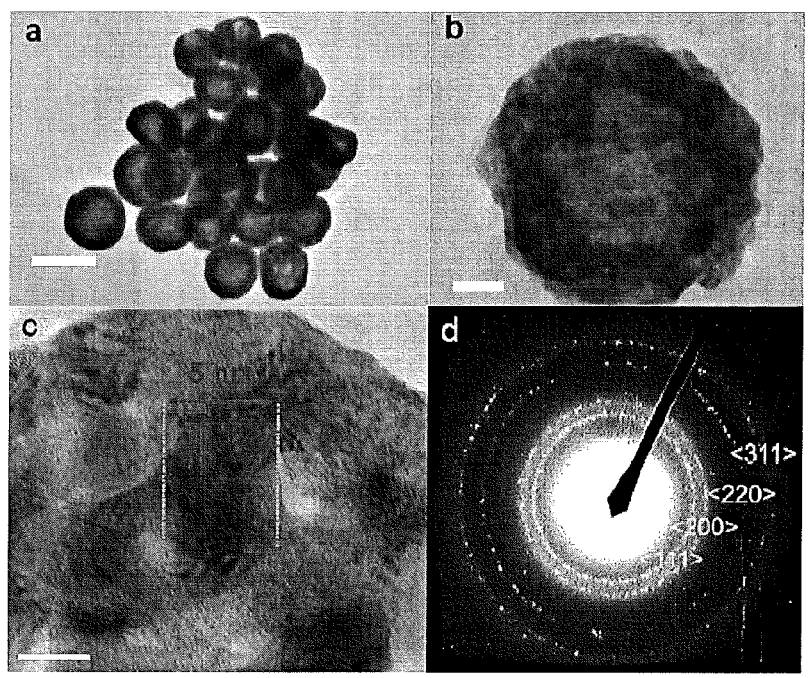
FIG. 5A is a transmission electron microscopy (TEM) image of hollow Au nanoparticles according to some embodiments described herein. Scale bar=100 nm.
FIG. 5B is a TEM image of a hollow nanoparticle according to some embodiments described herein. Scale bar=10 nm.
FIG. 5C is a TEM image of a hollow nanoparticle according to some embodiments described herein. Scale bar=5 nm.
FIG. 5D is a selected area electron diffraction (SAED) pattern of hollow Au nanoparticles according to some embodiments described herein.
Figure 6:
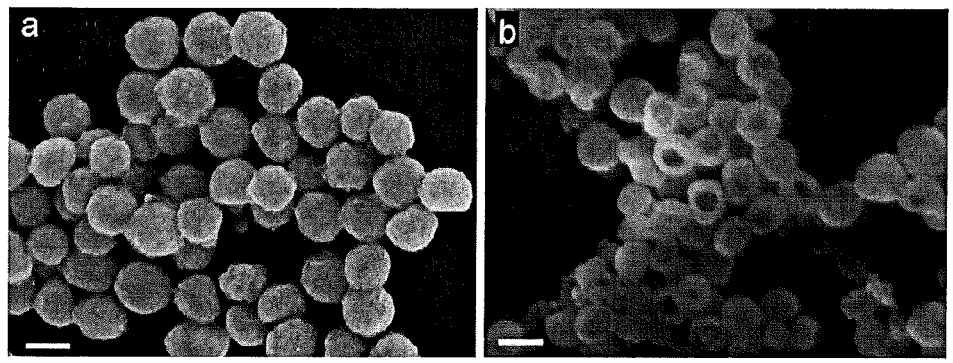
FIG. 6A is an SEM image of hollow Au nanoparticles according to some embodiments described herein, before ion milling. Scale bar=100 nm.
FIG. 6B is an SEM image of hollow Au nanoparticles according to some embodiments described herein, after ion milling. Scale bar=100 nm.
Figure 7:
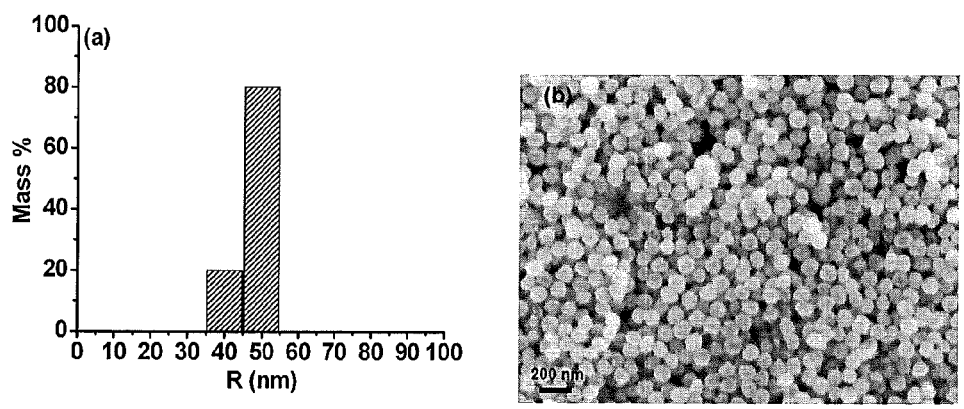
FIG. 7A is a plot of particle size distribution for a population of hollow Au nanoparticles according to some embodiments described herein, as measured by Dynamic Light Scattering (DLS). The mean radius is 53±5 nm.
FIG. 7B is an SEM image of hollow Au nanoparticles according to some embodiments described herein. Scale bar=200 nm.

The hollow Au nanoparticles were characterized using scanning electron microscopy (SEM), transmission electron microscopy (TEM), and dynamic light scattering (DLS). Bright field images and selective area electron diffraction (SAED) patterns were acquired using a Hitachi H9500 HR-TEM operating at 300 kV. Samples were prepared by placing a drop of hollow Au nanoparticle suspension on a carbon coated copper grid, waiting 10 minutes for the particles to settle on the grid, and then removing excess solution. FIG. 5 shows TEM micrographs (A-C) and a selected area diffraction pattern (D) of hollow Au nanoparticles. Ion milling was used to open the hollow Au nanoparticles for further characterization. SEM micrographs were taken using a ZEISS Supra 55 VP SEM. Samples were prepared by spreading diluted aqueous suspensions of hollow Au nanoparticles on a piece of silicon wafer, forming a monolayer of nanoparticles on the surface. Ion milling was performed using a Gatan Precision Ion Polishing System with 4.5 keV ion guns tilted at 4 degrees for 5 minutes. The two beam currents were 36 μA and 48 μA, and the sample was rotated at 4 rpm. FIG. 6 shows the treated hollow Au nanoparticles. FIG. 7 shows the size distribution of a population of hollow Au nanoparticles using DLS.

Example 2

Hollow Au Nanoparticles Formed Using a Patterned Substrate

Figure 8:
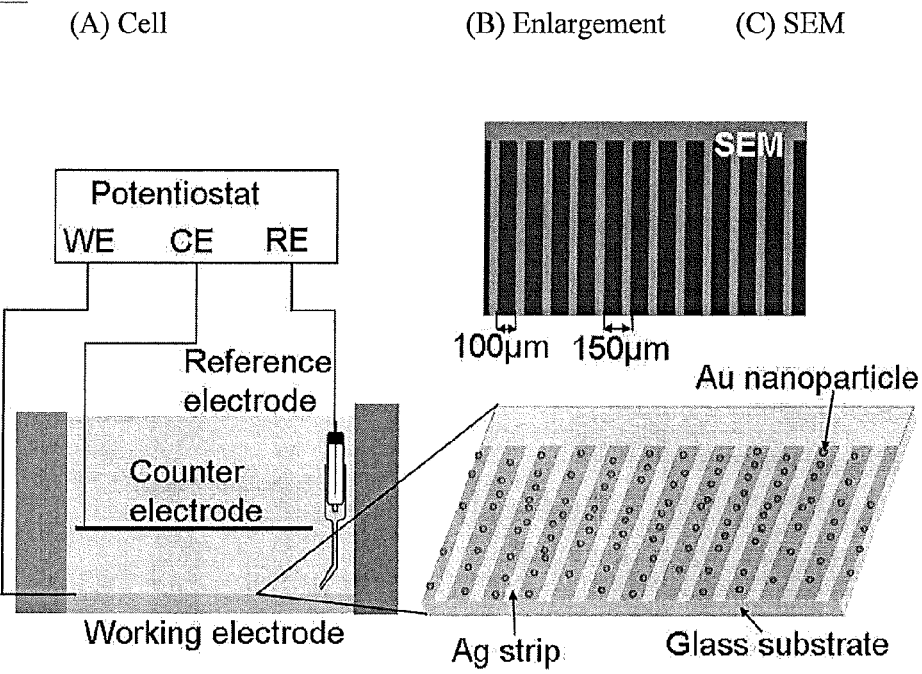
FIG. 8A illustrates a three-electrode cell suitable for use in some methods described herein.
FIG. 8B is an enlarged view of a silver/glass substrate in the cell of FIG. 8A.
FIG. 8C is an SEM image of a patterned substrate suitable for use in some methods described herein.
Figure 9:
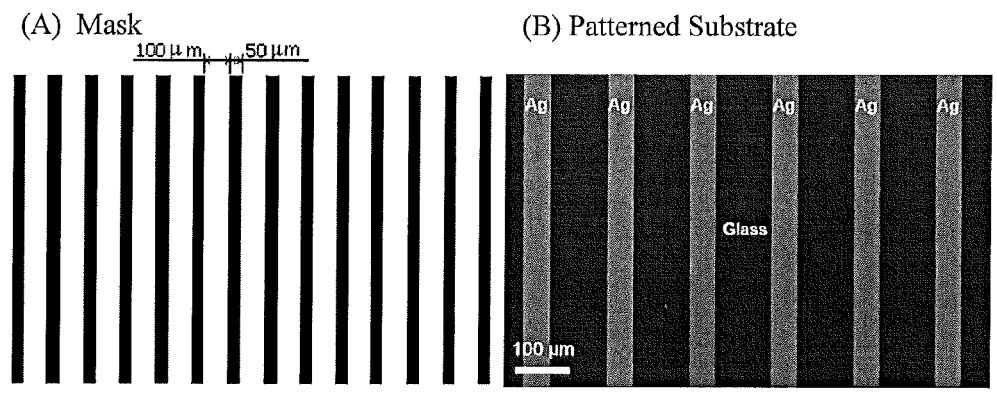
FIG. 9A shows a photolithography photomask pattern for a substrate suitable for use in some methods described herein.
FIG. 9B shows a patterned substrate suitable for use in some methods described herein, comprising silver (Ag) stripes on silica ($SiO_2$). Scale bar=100 μm.

Hollow Au nanoparticles consistent with some embodiments herein were provided as follows. The hollow Au nanoparticles were formed using a three-electrode cell with a Ag/AgCl electrode in 3 M NaCl solution as the reference and a platinum mesh as the counter electrode, as shown in FIG. 8. A lithographically patterned electrode consisting of Ag stripes on a glass substrate (an optical microscope slide) was used as the working electrode. The optical microscope glass slide was rinsed with deionized water and then cleaned with plasma treatment before use. Photolithography was used to pattern the glass substrate. The photomask design is shown in FIG. 9A. The width of the stripes was 50 μm, and the stripes were duplicated every 100 μm. The Ag stripe patterned substrate is shown in FIG. 9B. The uncoated glass regions of the substrate provided surfaces for the nucleation and growth of hollow Au nanoparticles. Potentials were applied to the working electrode using a Princeton Applied Research 273A Potentiostat/Galvanostat.

An electrolyte was disposed in the electrodeposition cell described above. Reagent grade chemicals used to prepare various electrolytes included the following. Aqueous sodium gold sulfite ($Na_3Au(SO_3)_2$) solution with a pH ~10.5 was purchased from Colonial Metals Inc., and diluted to 10% or 5% with deionized water. Ethylenediamine (EDA, 99%, Sigma-Aldrich) was diluted to 50% or 5% with deionized water. Aqueous solution of 0.4 M nickel sulfamate ($Ni(SO_3NH_2)_2$) with a pH ~5.8 was prepared using deionized water and 98% nickel sulfamate tetrahydrate ($Ni(SO_3NH_2)_2 \cdot 4H_2O$) purchased from Sigma-Aldrich. To prepare a series of electrolytes, the components indicated in Table 1 were mixed, and the electrolytes were further acidified with 5% sulfuric acid to reach a pH of about 6.

TABLE 1

| | Electrolytes. | | |
|---|---|---|---|
| Electrolyte | $Na_3Au(SO_3)_2$ (5%) | EDA (5%) | $Ni(SO_3NH_2)_2$ (0.4M) |
| 1 | 1 mL | | |
| 2 | 0.5 mL | 0.5 mL | |
| 3 | 0.5 mL | | 0.5 mL |
| 4 | 0.5 mL | 0.5 mL | 0.5 mL |

Figure 10:
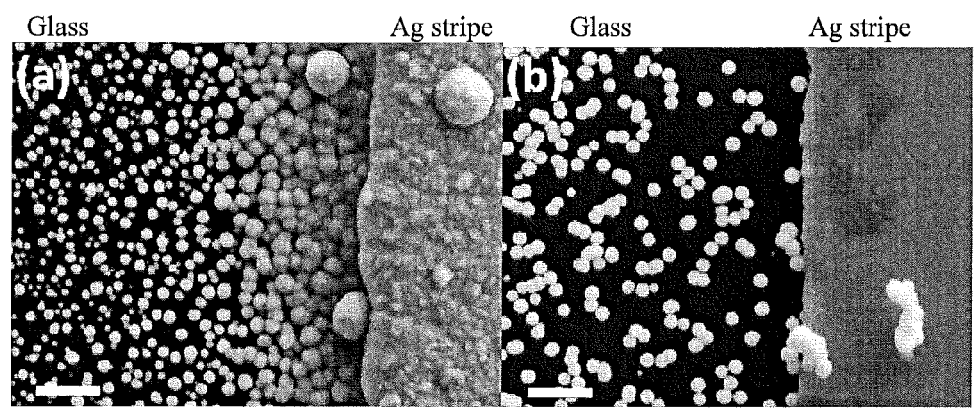
FIG. 10A is an SEM image of Au nanoparticles according to some embodiments described herein, on a Ag/$SiO_2$ substrate. Scale bar=1 μm.
FIG. 10B is an SEM image of Au nanoparticles according to some embodiments described herein, on a Ag/$SiO_2$ substrate. Scale bar=1 μm.

After disposing an electrolyte in the electrodeposition cell, a potential was applied. When a potential more negative than the hydrogen evolution equilibrium potential was applied to the Ag stripes, a large number of gold nanoparticles were formed on the glass areas, as shown in FIG. 10 (scale bar is 1 μm). The nanoparticles in FIG. 10A were formed using an electrolyte without $Ni^{2+}$. The nanoparticles in FIG. 10B were formed using an electrolyte including $Ni^{2+}$.

Example 3

Hollow Au Nanoparticles Using a TEM Grid

Figure 11:
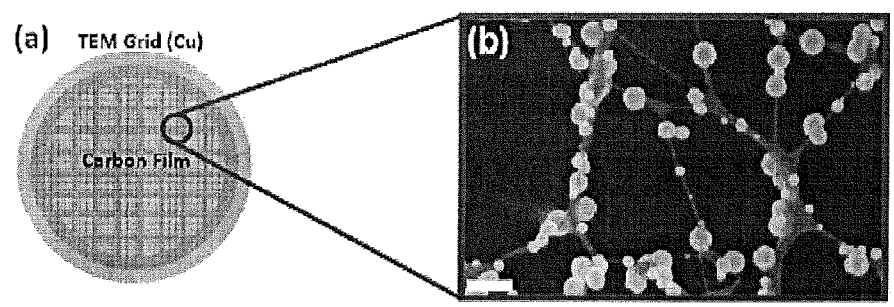
FIG. 11A illustrates a TEM grid suitable for use in some methods described herein, comprising copper mesh and carbon film.
FIG. 11B is an SEM image of Au nanoparticles according to some embodiments described herein, on the carbon film of a TEM grid suitable for use in some methods described herein. Scale bar=1 μm.
Figure 12:
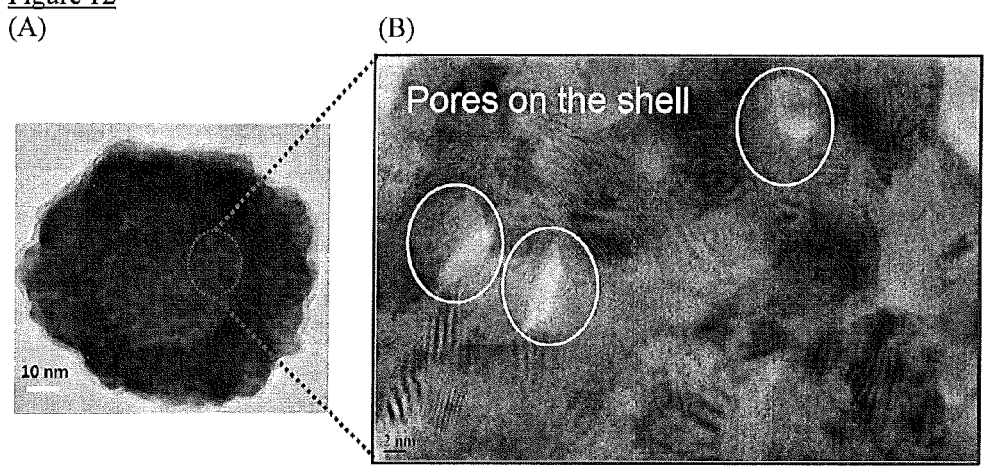
FIG. 12A is a TEM image of a hollow Au nanoparticle with a porous shell according to some embodiments described herein. Scale bar=10 nm.
FIG. 12B is a High Resolution TEM (HR-TEM) image of a hollow Au nanoparticle with a porous shell according to some embodiments described herein. Scale bar=2 nm.

Hollow Au nanoparticles consistent with some embodiments herein were provided as follows. The hollow Au nanoparticles were formed using a method similar to that described in Example 2, except a TEM grid was used as the working electrode and nucleation substrate. The TEM grid comprised a copper mesh coated with a carbon film. As shown in FIG. 11, hollow Au nanoparticles were observed on the carbon film. The scale bar is 1 μm. Characterization by high resolution TEM (HR-TEM) was carried out after the electrodeposition without any further treatment.

Example 4

Hollow Au Nanoparticles with a Porous Shell

Hollow Au nanoparticles consistent with some embodiments herein were provided as follows. The nanoparticles were formed using a method similar to that described in Example 1. An electrodeposition cell as described in Example 1 was used, except a stack of two instead of five anodic alumina filtration membranes was used, and a 700 nm layer of Cu was sputter deposited to block the pores of the bottom membrane and serve as the working electrode. A commercial Au sulfite solution (Techni-Gold 25 ES RTU from Technic, Inc.) was used as the electrolyte. The initial pH of the solution was about 7.0. The solution was altered by adding 0.4 M Ni sulfamate solution to change the pH to about 6.0. A potential of −0.80 V (vs. Ag/AgCl reference) was applied to the working electrode using a Princeton Applied Research 273A Potentiostat/Galvanostat. Hydrogen evolution occurred at this potential. To obtain hollow Au nanoparticles having a porous shell, the reaction time was held to less than 10 minutes. The hollow Au nanoparticles with porous shells were purified and isolated as described in Example 1.

Example 5

Hollow Au Nanoparticles Comprising Hollow Au Nanoparticles

Figure 13:
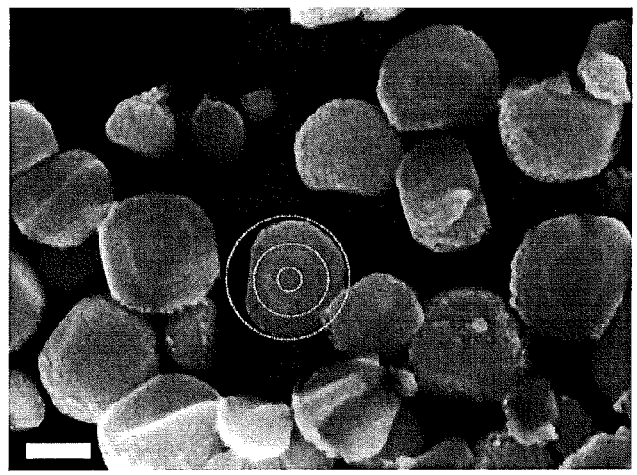
FIG. 13 is an SEM image of double-shell nanoparticles according to some embodiments described herein, after ion milling treatment. Scale bar=200 nm.
Figure 14:
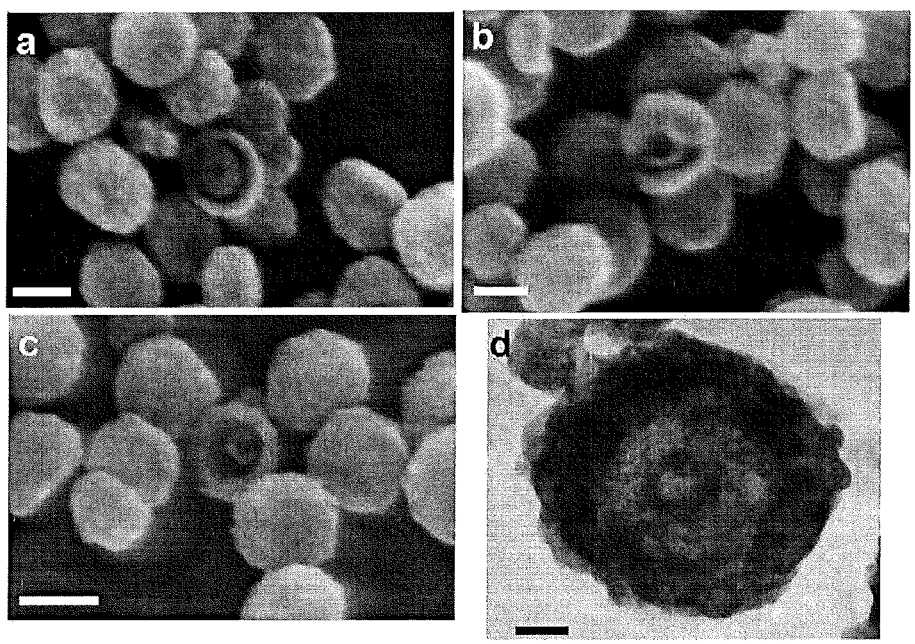
FIG. 14A is an SEM image of double-shell nanoparticles according to some embodiments described herein. Scale bar=100 nm
FIG. 14B is an SEM image of double-shell nanoparticles according to some embodiments described herein. Scale bar=100 nm.
FIG. 14C is an SEM image of double-shell nanoparticles according to some embodiments described herein. Scale bar=100 nm.
FIG. 14D is a TEM image of a double-shell nanoparticle according to some embodiments described herein. Scale bar=20 nm.

Hollow Au nanoparticles consistent with some embodiments herein were provided as follows. The hollow Au nanoparticles were formed using a method similar to that described in Example 1, except the applied potential was pulsed. Fabrication of nanoparticles was initiated with an applied potential of −0.8 V (vs. Ag/AgCl) for 600 seconds followed by an open circuit for 300 seconds. The pulse potential was repeated for two additional cycles. Double-shell nanoparticles were obtained, as shown in FIG. 13. The average diameter of the inner cavities was about 50 nm, and the overall size was about 300 nm. The scale bar is 200 nm. Other double-shell nanoparticles are shown in FIG. 14. The scale bar in FIG. 14A-C is 100 nm. The scale bar in FIG. 14D is 20 nm.

Example 6

Hollow Au Nanoparticles Comprising $Fe_3O_4$ Nanoparticles

Hollow Au nanoparticles comprising $Fe_3O_4$ nanoparticles consistent with some embodiments herein were provided as follows. Hollow Au nanoparticles with porous shells were prepared in a manner similar to that described in Example 4. The pH value of the electrolyte was adjusted with 0.2 M sodium sulfite to reach a pH of about 6.5, and the reaction time was between 400 and 600 seconds. The resulting hollow Au nanoparticles had a cavity about 50 nm in diameter and a shell less than about 25 nm thick. The shell was porous and exhibited pore sizes of about 2-3 nm, as measured by HR-TEM.

Figure 15:
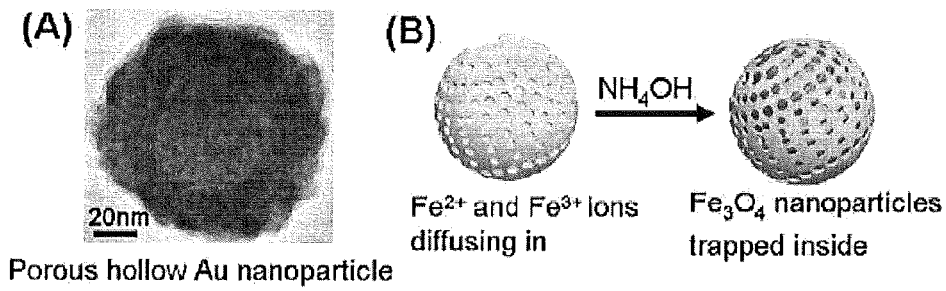
FIG. 15A is a TEM image of a porous nanoparticle according to some embodiments described herein. Scale bar=20 nm.
FIG. 15B illustrates a method of making a composite particle according to one embodiment described herein.

To produce iron oxide nanoparticles within the hollow Au nanoparticles, 5.2 g (0.032 mol) anhydrous $FeCl_3$ and 2 g (0.016 mol) $FeCl_2$ were added under vigorous stirring to 25 mL deionized water containing 0.85 mL HCl (12.1 N). After this, the mixed solution of $FeCl_2$ and $FeCl_3$ in HCl was diluted 40 times with deionized water. The resulting aqueous solution was delivered into the channels of an alumina membrane loaded with the hollow Au nanoparticles described above using vacuum filtration, where the alumina membrane served as the "filter" in the vacuum filtration procedure. The wetted alumina membrane was then immersed in the $FeCl_3/FeCl_2$ solution for about 30 minutes. The membrane was then transferred into 5 mL of 30% $NH_4OH$ aqueous solution and left there for an additional 10-20 minutes. A yellow-orange color appeared, indicating the formation of iron oxide nanoparticles. Free iron oxide nanoparticles (about 10 nm in diameter) formed inside the alumina membrane but outside the hollow Au nanoparticle cavities were removed by passing deionized water through the membrane under vacuum filtration. The membrane was then dissolved using 1-2 M NaOH (aq.), and $Fe_3O_4$/Au core/shell nanoparticles were released into solution. The nanoparticles were purified by several cycles of dispersion in deionized water followed by centrifugation. This process is depicted in FIG. 15.

Figure 16:
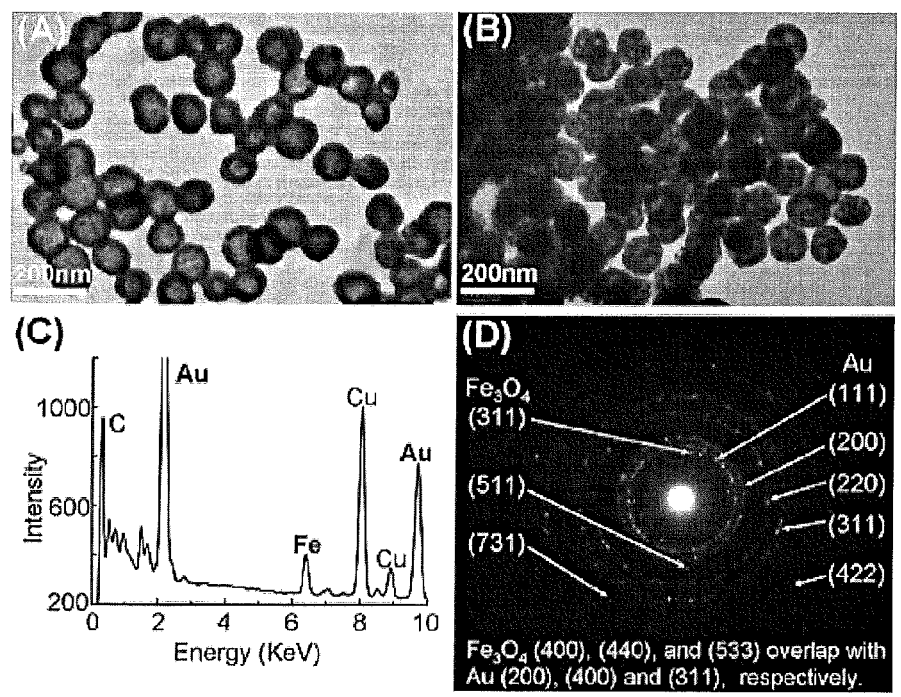
FIG. 16A is a TEM image of porous nanoparticles according to some embodiments described herein, before loading with other nanoparticles, according to some embodiments described herein. Scale bar=200 nm.
FIG. 16B is a TEM image of the nanoparticles of FIG. 16A after loading, according to some embodiments described herein. Scale bar=200 nm.
FIG. 16C is an energy dispersive x-ray spectroscopy (EDS) spectrum of one composite nanoparticle from FIG. 16B.
FIG. 16D is an SAED pattern of three composite nanoparticles from FIG. 16B.

The composite nanoparticles were characterized by energy dispersive x-ray spectroscopy (EDS) and TEM, including selected area electron diffraction (SAED). The optical and magnetic properties of the composite particles were also examined. FIG. 16 shows TEM images (FIG. 16A) before and (FIG. 16B) after loading of iron oxide nanoparticles into the hollow Au nanoparticles. During the precipitation of $Fe_3O_4$ nanoparticles within the cavity of the hollow Au nanoparticles, $Fe_3O_4$ nanoparticles also formed outside of the cavity. But the TEM images indicated that no small iron oxide nanoparticles were attached to the outer surface of the hollow Au nanoparticles. The free (i.e., not trapped within a hollow Au nanoparticle cavity) $Fe_3O_4$ nanoparticles were less than 20 nm in diameter and were readily separated from the $Fe_3O_4$/Au composite particles using filtration and centrifugation. The loading of $Fe_3O_4$ into the core of porous hollow Au nanoparticles was confirmed by EDS analysis of a single composite particle (FIG. 16C) and the selected area electron diffraction (SAED) pattern derived from three composite particles (FIG. 16D).

Figure 17:
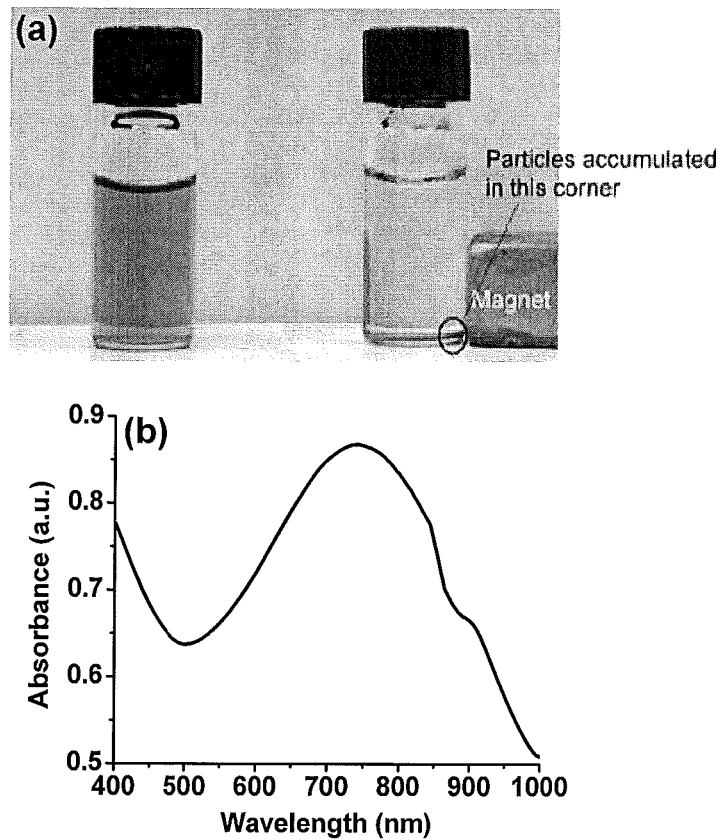
FIG. 17A is a series of photographs of a vial containing composite nanoparticles according to some embodiments described herein.
FIG. 17B is an absorption spectrum of an aqueous suspension of nanoparticles according to some embodiments described herein.

An aqueous suspension of $Fe_3O_4$/Au composite particles is shown in FIG. 17A. The suspension was cyan colored, indicating that the suspension absorbed red light. The absorption peak shown in FIG. 17B corresponded to the SPR wavelength of the hollow Au nanoparticles. The absorption profile of the hollow Au nanoparticles varied little before and after $Fe_3O_4$ loading. Not intending to be bound by theory, the maintenance of the absorption profile might have been due to the thickness of the Au shell (>20 nm). Therefore it was possible to independently select and maintain the optical properties of the hollow nanoparticle host.

Figure 18:
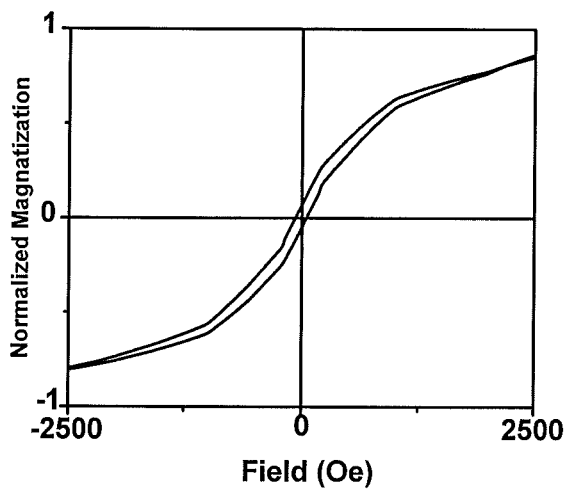
FIG. 18 is a hysteresis loop of a dried powder of nanoparticles according to some embodiments described herein.

Further, as shown in FIG. 17A, the composite particles could be dragged towards a permanent magnet. The magnetization curve of a dried power comprising the $Fe_3O_4$/Au composite particles exhibited hysteresis, as shown in FIG. 18. The shape of the curve suggested the presence of some smaller (<20 nm), superparamagnetic $Fe_3O_4$ nanoparticles as well as some larger (>30 nm), ferromagentic $Fe_3O_4$ nanoparticles within the cavities of the hollow Au nanoparticles.

Example 7

Hollow Au Nanoparticles Comprising Doped $Fe_3O_4$ Nanoparticles

Figure 19:
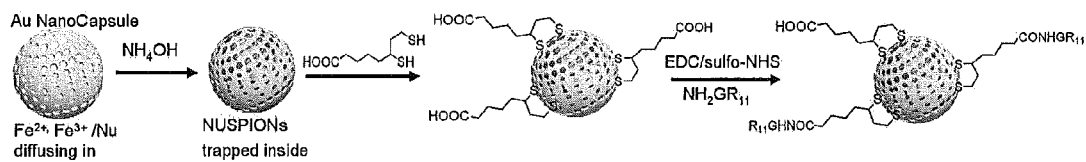
FIG. 19 illustrates a method of making composite particles according to one embodiment described herein.

Hollow Au nanoparticles comprising doped $Fe_3O_4$ nanoparticles consistent with some embodiments herein are provided as follows. Hollow Au nanoparticles comprising $Fe_3O_4$ nanoparticles are prepared in a manner similar to that described in Example 6, except a source of dopant ions is also provided along with sources of $Fe^{2+}$ and $Fe^{3+}$ ions. The dopant ions include nuclides useful for positron emission tomography (PET) imaging, such as $^{64}Cu^{2+}$ or $^{89}Zr^{4+}$. Once the Au/doped $Fe_3O_4$ nanocomposites are prepared and purified in a manner similar to that described in Example 6, the surfaces are functionalized as follows. Prior to dissolution of the alumina membrane, a solution of lipoic acid or dihydrolipoic acid (DHLA) is added to the membrane resulting in the association of this ligand with the hollow Au nanoparticle surface. The membrane is then further rinsed with deionized water. The carboxylic acid groups of the lipoic acid/DHLA ligands are then coupled to $NH_2GR_{11}$ using carbodiimide coupling with N-(3-dimethylaminopropyl)-N"-ethylcarbodiimide hydrochloride (EDC) and N-hydroxysulfosuccinimide (sulfo-NHS), where $NH_2GR_{11}$ is a prostate cancer specific polyarginine peptide described, for example, in Gao et al., *Amino Acids*, 2010 Mar. 11: 20221650, which is hereby incorporated by reference in its entirety. The nanocomposite particle comprising the peptide targeting agent is then purified by size exclusion high performance liquid chromatography (HPLC) or three cycles of centrifugation filtration using centricon filters with a molecular weight cutoff of about 30 kDa. This process is depicted in FIG. 19.

Example 8

Hollow Au Nanoparticles Comprising a Therapeutic Agent

Hollow Au nanoparticles consistent with some embodiments herein are provided as follows. Hollow Au nanoparticles with porous shells are prepared in a manner similar to that described in Example 4 or Example 6. Then an alumina membrane loaded with the porous hollow Au nanoparticles is immersed into a concentrated solution of a therapeutic agent, such as a drug. The membranes are kept in the solution for a sufficient time (such as 10-600 minutes) to allow diffusion of the therapeutic agent into the Au nanoparticle cavities. Then a metal-containing precursor, such as $Na_3Au(SO_3)_2$, is added to the solution in the membrane to allow the porous Au shell to grow, sealing at least some of the pores. The resulting hollow Au nanoparticles comprising a therapeutic agent can then be used for medical treatment. The encapsulated therapeutic agent is released by rupturing the Au shell. The shell is ruptured by irradiating the shell with light having a wavelength at or near the SPR frequency of the shell.

Example 9

Hollow Au Nanoparticles Comprising a Raman Active Species

Figure 20:
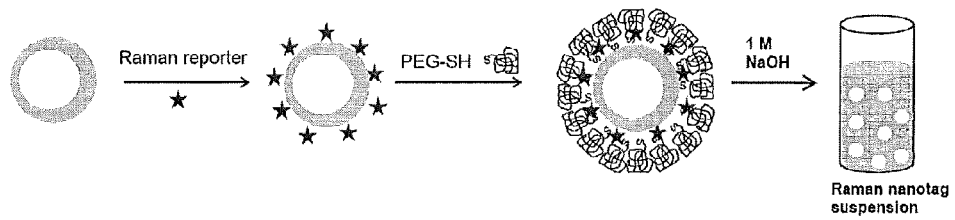
FIG. 20 illustrates a method of making nanoparticles according to one embodiment described herein.

Hollow Au nanoparticles consistent with some embodiments herein were provided as follows. Hollow gold nanoparticles were synthesized as described in Example 4. The hollow gold nanoparticles had a cavity diameter of about 50 nm and an outer diameter of about 100 nm, with an absorption peak centered at 730 nm. An anodic aluminum oxide membrane containing about $1.1 \times 10^{11}$ nanoparticles/mL was immersed in a freshly made 20 mL solution of 5 µM diethylthiatricarbocyanine (DTTC) Raman reporter dye and kept there for 3 hours at room temperature. The alumina membrane was then rinsed with deionized water several times. The nanoparticle-loaded membrane was then immersed overnight in a solution of 20 µM SH-mPEG (MW 5 kDa, where mPEG refers to methoxy polyethylene glycol) at 4° C. The alumina membrane was then dissolved using 1 M NaOH solution. The nanoparticles were purified by several cycles of dispersion in deionized water followed by centrifugation. This process is illustrated in FIG. 20.

Figure 21:
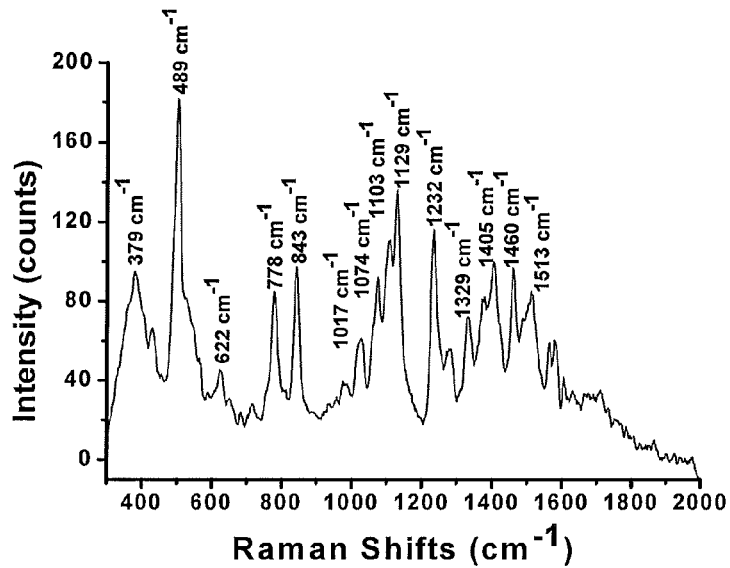
FIG. 21 is a Raman spectrum of a composite particle according to some embodiments described herein.
Figure 22:
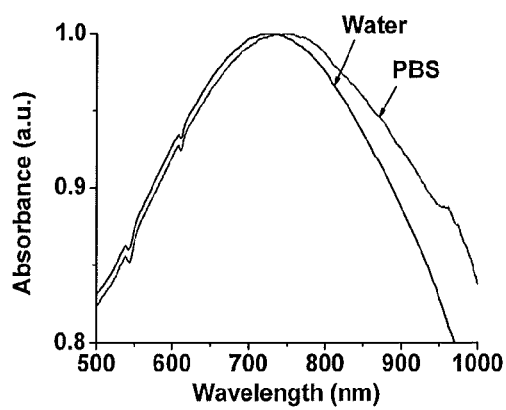
FIG. 22 is a comparison of the absorption spectra of nanoparticles according to some embodiments described herein, in water and in 10 mM phosphate buffered saline (PBS).
Figure 23:
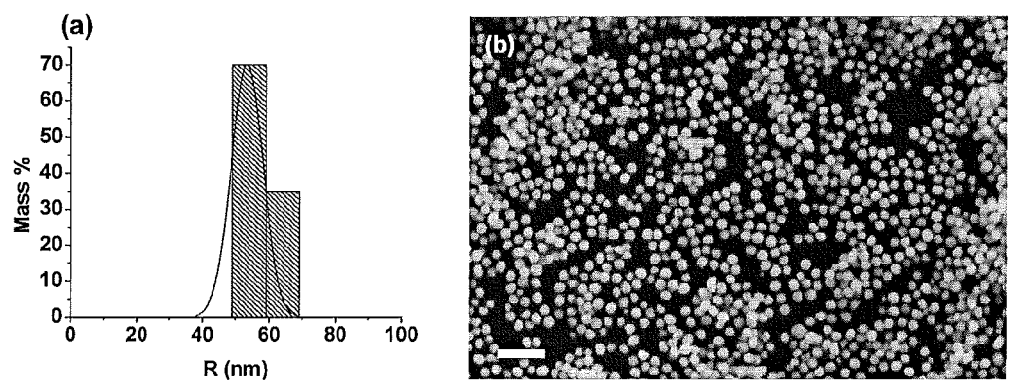
FIG. 23A is a plot of the particle size distribution of nanoparticles according to some embodiments described herein, measured by DLS.
FIG. 23B is an SEM image of nanoparticles according to some embodiments described herein. Scale bar=5 nm.

The resulting hollow Au nanoparticles comprising a Raman active species, also referred to as "Raman nanotags," were characterized by Raman spectroscopy. Raman spectroscopy measurements were conducted in a home-made setup with 785 nm laser light. The laser light was propagated through an optical fiber (600 µm, NA=0.39) to a Raman module. At the Raman module, the light from this fiber was attenuated by a neutral density filter (ND=0.2) and collimated before it was incident on a dichotic which reflected the light onto a 20×, 0.4 NA objective lens with a working distance of 8.4 cm. The cell containing the Raman nanotag suspension was placed at the focus of this lens for surface enhanced Raman spectroscopy (SERS) measurement. Light reflected and scattered by the suspension was collected by the objective and transmitted by the dichotic to a notch filter before being focused by a 10×, 2.5 NA lens into an optical fiber (600 µm, NA=0.39) which then propagateed the light to a spectrometer. Spectra were acquired with an exposure time of 8 seconds. The Raman spectra of a 50 µL solution of Raman nanotags with a concentration of $5.8 \times 10^{10}$ nanoparticles/mL exhibited the major vibrational modes of DTTC at 379, 489, 622, 778, 843, 1017, 1074, 1103, 1129, 1232, 1329, 1405, 1460 and 1513 $cm^{-1}$, as shown in FIG. 21. The Raman nanotags were stable in 10 mM phosphate buffered saline (PBS), as shown in FIG. 22. The Raman nanotags were also stable in 3 M NaCl at room temperature for up to one month. No aggregation was observed by UV-vis spectroscopy. The size of the Raman nanotags was measured by DLS in PBS. As shown in FIG. 23, the measured size in PBS was about 10 nm greater than the size indicated by SEM. The scale bar is 500 nm.

The cytotoxicity of the Raman nanotags was evaluated using the PC-3 cell line, a human prostate cancer cell line (American Type Culture Collection, Manassas, Va.). Cells were maintained in GIBCO's T-medium supplemented with 5% FBS (fetal bovine serum), and 1× Penicillin/Streptomycin. Cells were incubated at 37° C. in a 5% $CO_2$ environment and were passed at 75% confluence in P150 plates. The cultured PC-3 cells were harvested from monolayer using PBS and trypsin/EDTA and suspended in T-media with 5% FBS. The cytotoxicity evaluation was performed using [$^3$H]-thymidine incorporation, which is a measurement of DNA synthesis rate as a marker for cell proliferation. Approximately 3000 cells were seeded in a flat-bottomed 96-well polystyrene coated plate and incubated for 24 hours at 37° C. in a 5% $CO_2$ incubator. The hollow gold nanoparticles with different coatings (PEG only versus Raman reporter dye with PEG) were suspended in the T-medium. The evaluated concentrations were 960, 480, 96, and 9.6 mM. The hollow gold nanoparticle-loaded T-medium was added to the plate in hexaplets. After 24 hours of incubation of cells and nanoparticles, the T-medium was aspirated from each well, and the cell layer was rinsed 3 times with complete growth T-medium and then [³H]-thymidine solution (1 µCi/100 µL T-medium) was added to each well. After 2 hours incubation, the medium was aspirated from each well and the cell layer was rinsed 3 times with complete growth T-medium. The cells were then solubilized with 100 µL of 2 N NaOH solution. The solutions were collected from the wells and added to scintillation vials containing 5 mL of Budget-Solve Complete Counting Cocktail. Finally, [³H]-thymidine incorporated into DNA was quantified by Liquid Scintillation β-Counter (Beckman LS 6500). Statistically, the treated cells showed the same viability as the control.

Example 10

Hollow Au Nanoparticles Comprising a Targeting Species

Hollow Au nanoparticles consistent with some embodiments herein were provided as follows. Raman nanotags were prepared as described in Example 9, except addition of the Raman reporter dye and polyethylene glycol was carried out as follows. A freshly prepared solution of Raman reporter dye was flowed through the alumina membrane loaded with porous hollow Au nanoparticles followed by the flow through the membrane of a mixture of SH-mPEG (10 µM, MW 5 kDa) and SH-PEG-COOH (1 µM, MW 2 kDa) solutions at a volumetric ratio of 2:7. To a 1 mL solution of the purified Raman nanotags, EDC and sulfo-NHS were added and incubated for 30 minutes. The composite particles were then purified by three cycles of centrifugation followed by redispersion in PBS. Anti-PSMA (where "PSMA" refers to a type II transmembrane glycoprotein overexpressed in prostate cancers) was then added to the solution of activated ester nanotags, and the mixture was allowed to react at 4° C. overnight. The resulting antibody-nanotag conjugate was purified by either size exclusion column separation or centricon centrifugation.

Example 11

Hollow Au Nanoparticles with a Roughened Surface

Figure 24:
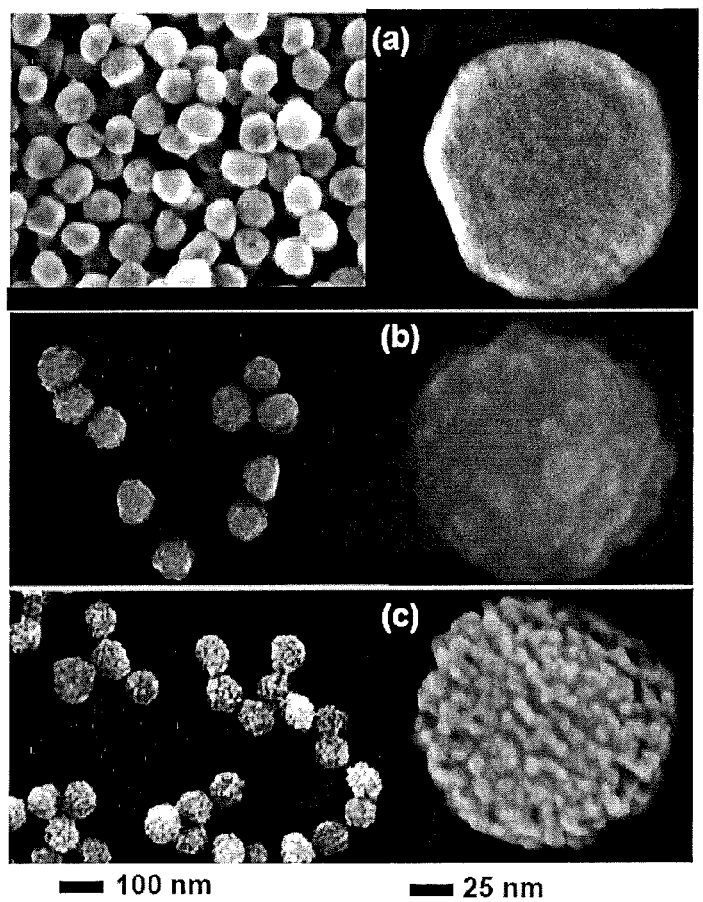
FIG. 24A is an SEM image of hollow Au nanoparticles according to some embodiments described herein.
FIG. 24B is an SEM image of hollow Au nanoparticles according to some embodiments described herein.
FIG. 24C is an SEM image of hollow Au nanoparticles according to some embodiments described herein.
Figure 25:
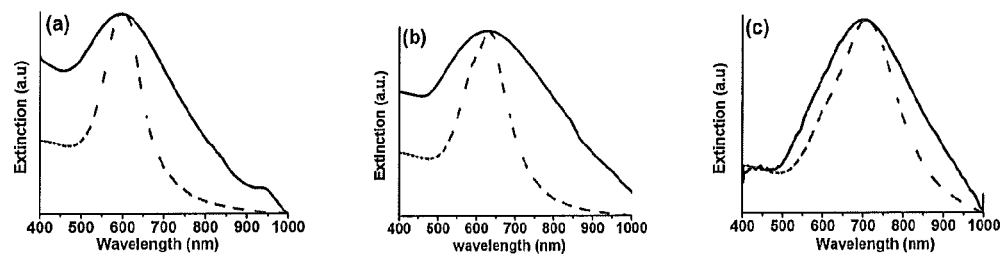
FIG. 25A is a comparison of experimental (solid line) and simulated (dashed line) absorption spectra of hollow Au nanoparticles according to some embodiments described herein.
FIG. 25B is a comparison of experimental (solid line) and simulated (dashed line) absorption spectra of hollow Au nanoparticles according to some embodiments described herein.
FIG. 25C is a comparison of experimental (solid line) and simulated (dashed line) absorption spectra of hollow Au nanoparticles according to some embodiments described herein.

Hollow Au nanoparticles consistent with some embodiments herein were provided as follows. Hollow Au nanoparticles having a roughened surface were prepared in a manner similar to that described in Example 1, except the pH of the electrolyte was altered as follows. Hollow Au nanoparticles prepared using an electrolyte with a pH of about 6.0 exhibited relatively smooth shells. To increase the surface roughness, the pH of the electrolyte was increased to about 6.5 or 7.0 through the addition of 2 M $Na_2SO_3$ (pH about 9.0). Not intending to be bound by theory, the pH dependence of the roughness can be attributed to the increase in the rate of the autocatalytic reaction of $Na_3Au(SO_3)_2$ (and thus grain growth and final grain size) with pH. FIG. 24 shows the surface morphology of hollow gold nanoparticles synthesized using electrolytes with different pH values. FIG. 24A shows a smooth shell formed at an electrolyte pH of about 6.0. FIG. 24B shows a shell having a surface roughness of about 5 nm and formed at an electrolyte pH of about 6.5. FIG. 24C shows a shell having a surface roughness of about 8 nm and formed at an electrolyte pH of about 7.0. FIG. 25 shows the corresponding absorption spectra of aqueous suspensions of the hollow Au nanoparticles. The dashed lines in FIG. 25 correspond to simulated absorption profiles. The plasmon peak shifted to longer wavelength with the increase of electrolyte pH. When the pH changed from about 6.0 to 6.5 to 7.0, the SPR peaks shifted from about 600 nm to 630 nm to 730 nm.

Example 12

Hemispherical and Tubular Au Nanoparticles

Figure 26:
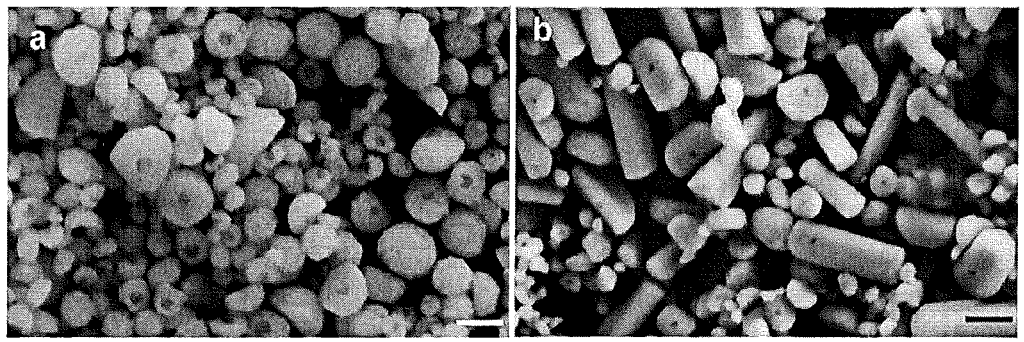
FIG. 26A is an SEM image of nanoparticles according to some embodiments described herein. Scale bar=100 nm.
FIG. 26B is an SEM image of nanoparticles according to some embodiments described herein. Scale bar=100 nm.

Hemispherical and tubular Au nanoparticles consistent with some embodiments herein were provided as follows. An electrochemical deposition cell similar to that described in Example 1 was used. An electrolyte was disposed in the electrodeposition cell. The electrolyte was prepared by first preparing an aqueous solution composed of ~3% sulfuric acid, ~3% ethylenediamine (EDA), ~10% sodium gold sulfite ($Na_3Au(SO_3)_2$), and ~7% sodium sulfite ($Na_2SO_3$). The solution had a pH of about 7.0. The solution was then altered by adding 0.01 M sulfuric acid ($H_2SO_4$) to reduce the pH to about 4.0. After disposing the electrolyte in the electrodeposition cell, a potential more negative than −0.6 V (vs. Ag/AgCl) was applied for about 10-60 minutes. With a deposition time of about 10 minutes, hemispherical gold nanoparticles were observed on the pore walls (FIG. 26A). With a deposition time of about 60 minutes, tubular nanoparticles were observed (FIG. 26B). The scale bars in FIG. 26 are 200 nm. Not intending to be bound by theory, it is believed that nanoparticle morphology is affected by the contact angle of $H_2$ bubbles on the pore wall surface, which is in turn affected by the hydrophobicity of the pore wall surface.

Example 13

Photothermal Properties of Hollow Au Nanoparticles

Figure 27:
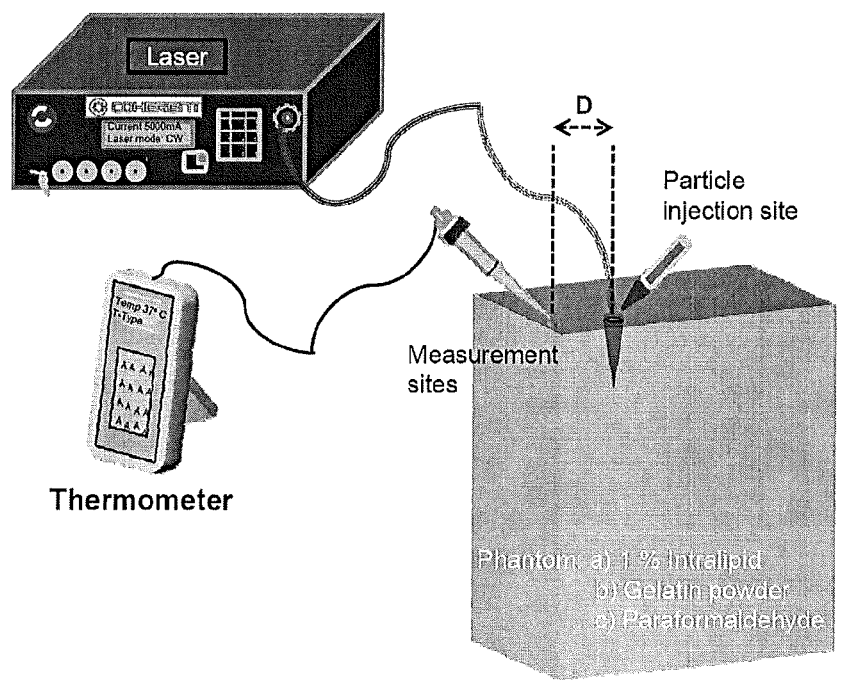
FIG. 27 illustrates an experiment for measuring photothermal properties according to some embodiments described herein.

The photothermal properties of hollow Au nanoparticles in tissue-like phantoms under near infrared (NIR) laser irradiation were investigated. Gel phantoms were prepared using 1% Intralipid, gelatin powder, and paraformaldehyde. Briefly, 2400 mg of highly purified gelatin powder was mixed with 228 mL of deionized water. The mixture was then heated by microwave for 2-4 minutes (to about 900° C.) with intermittent mixing until the gelatin was dissolved and the solution appeared clear and colorless. With continuous mixing at room temperature, the gelatin solution was permitted to cool to 600° C., at which time 12 mL of 1% Intralipid (20% fat emulsion, Sigma-Aldrich) and 140 mg paraformaldehyde (95%, Sigma-Aldrich) were added, which caused the solution to become white and opaque. After formation of the gel phantom, a thin pocket was created in the phantom. A suspension of hollow Au nanoparticles (50 µL, $3.0 \times 10^9$ nanoparticles/mL) having a SPR peak centered at 750 nm was disposed in the pocket via pipet. A diode laser fiber (mean wavelength of 810 nm) was also placed in the center of the pocket in contact with the nanoparticle suspension. The laser fiber was used to irradiate the hollow Au nanoparticles. The temperature change in the phantom was recorded by thermometer as a function of distance and time. FIG. 27 illustrates the experimental setup.

Figure 28:
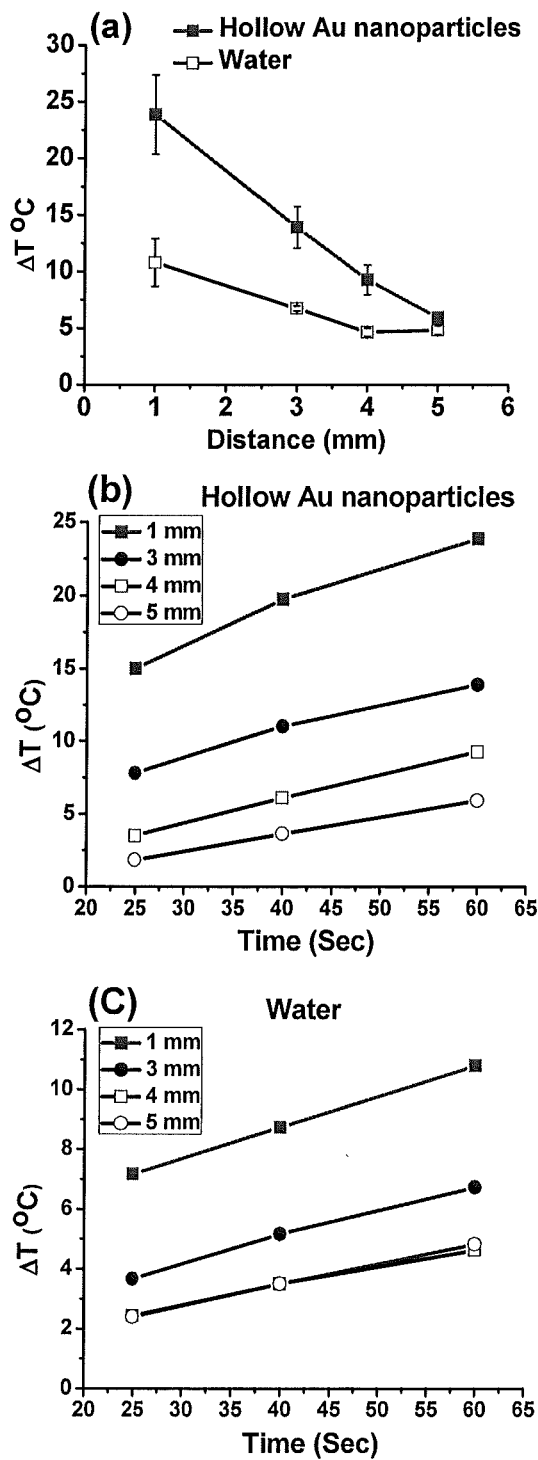
FIG. 28A is a comparison of some photothermal properties of hollow Au nanoparticles according to some embodiments described herein, and water at different measurement distances.
FIG. 28B is a comparison of some photothermal properties of hollow Au nanoparticles according to some embodiments described herein, measured at different distances and times.
FIG. 28C is a comparison of some photothermal properties of water measured at different distances and times.

Irradiation from the NIR diode laser was carried out for 1 minute at a power density of 300 W/cm². With 1 minute irradiation time, the temperature rose by 23, 13, and 8 degrees Celsius at a distance of 1, 3, and 4 mm from the irradiation point, respectively. Because water also absorbs at 810 nm, control experiments were conducted using water rather than a suspension of hollow Au nanoparticles. The temperature increase in the control experiments was 12, 7, and 5 degrees Celsius at a distance of 1, 3, and 4 mm, respectively. The results are shown in FIG. 28.

Figure 29:
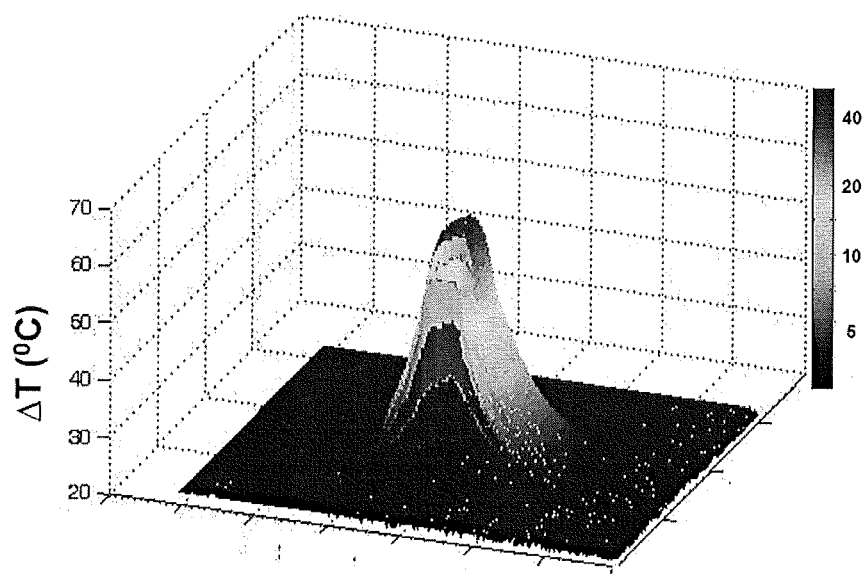
FIG. 29 is an infrared absorbance image of a cuvette containing hollow Au nanoparticles according to some embodiments described herein.
Figure 30:
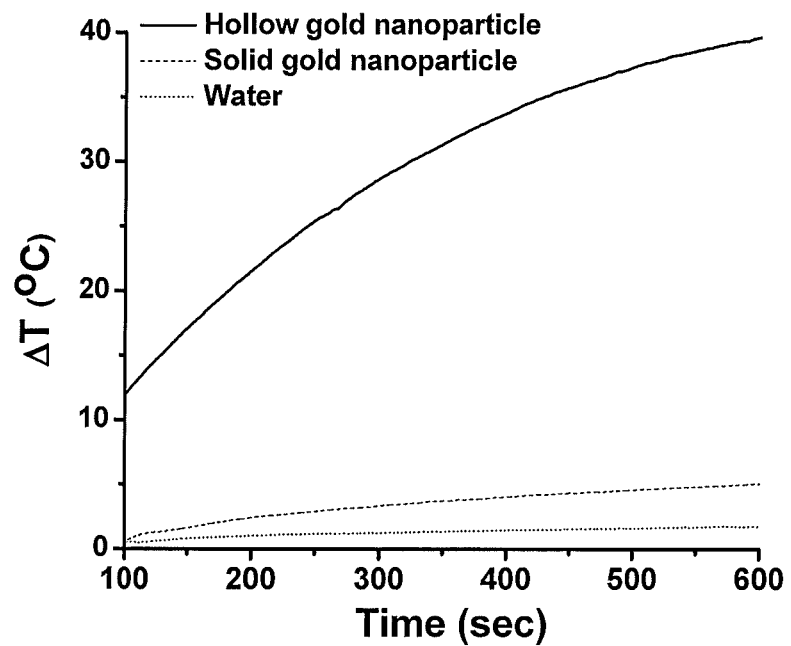
FIG. 30 is a comparison of temperature increases associated with solid Au nanoparticles, hollow Au nanoparticles according to some embodiments described herein, and water.
Figure 31:
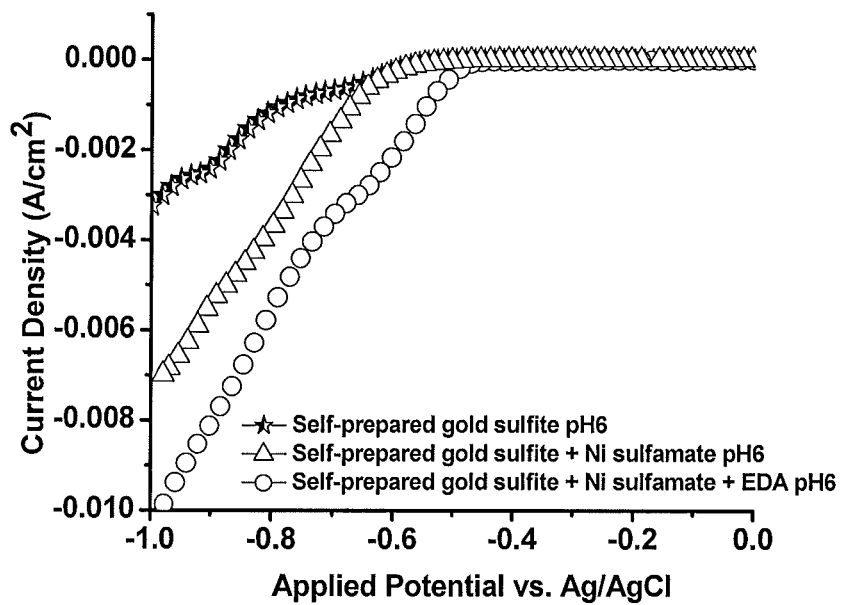
FIG. 31 is a series of cyclic voltammetry measurements. Data was recorded from the open circuit potential to −1.0 V (vs. Ag/AgCl) at a scan rate of 5 mV/s. The measurements were of different electrolytes including 10% sodium gold sulfite ($Na_3Au(SO_3)_2$) (aq.) and exhibiting a pH of about 6. The electrolyte associated with the data marked with triangles further included nickel sulfamate ($Ni(SO_3NH_2)_2$). The electrolyte associated with the data marked with circles further included $Ni(SO_3NH_2)_2$ and ethylenediamine (EDA).
Figure 32:
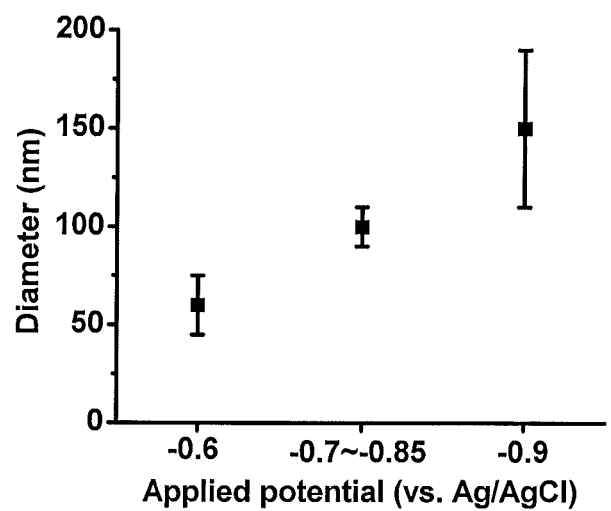
FIG. 32 is a plot of hollow Au nanoparticle size according to some embodiments described herein, against applied potential.
Figure 33:
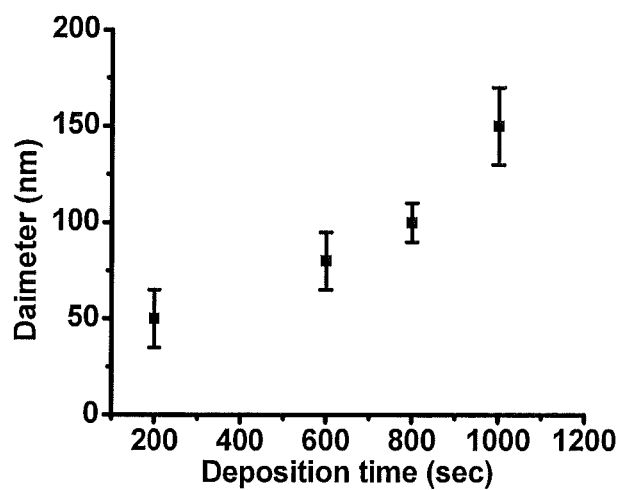
FIG. 33 is a plot of hollow Au nanoparticle size according to some embodiments described herein, against reaction time.
Figure 34:
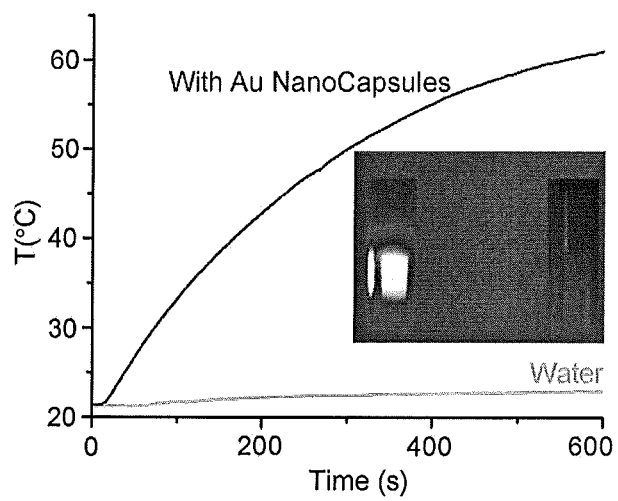
FIG. 34 is a comparison of the measured temperature of a cuvette of water and a cuvette containing an aqueous suspension of hollow Au nanoparticles ($1.9 \times 10^9$ particles per mL) according to some embodiments described herein, as a function of irradiation time, where irradiation was carried out using a near infrared (NIR) laser (800 nm) directed at the center of the cuvette with an incident laser power of 350 mW and a 3 mm diameter collimated Gaussian beam. The incident light flux was 1.2 W/cm². The temperature increase of the cuvette containing hollow Au nanoparticles according to some embodiments described herein, was 38 degrees after 10 minutes irradiation.
Figure 35:
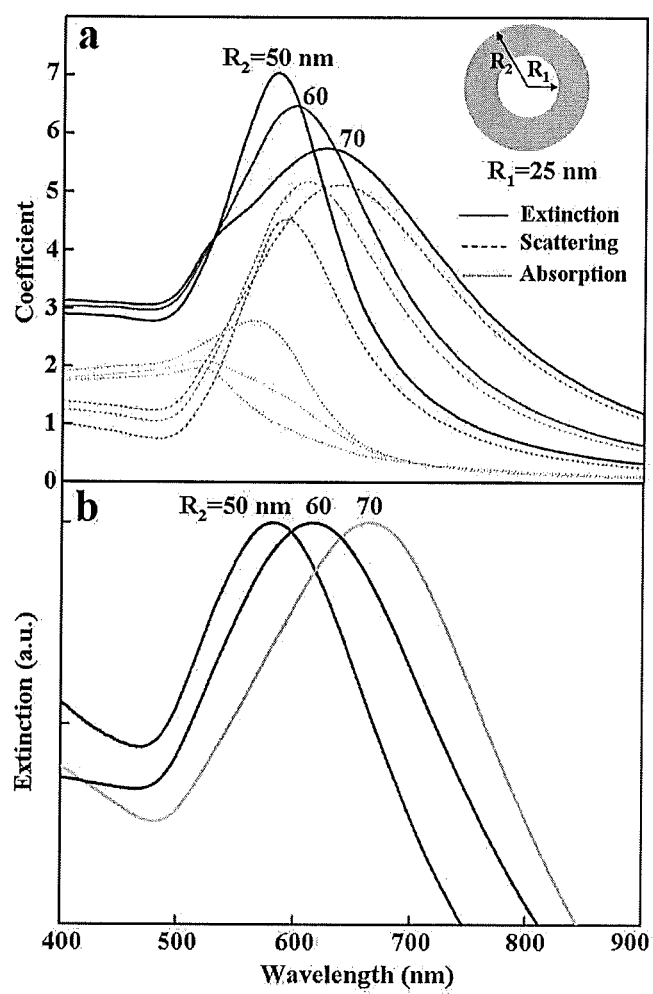
FIG. 35A shows the calculated total extinction, scattering and absorption efficiency for concentric hollow nanospheres using Mie theory.
FIG. 35B shows measured absorption spectra of hollow Au nanoparticles according to some embodiments described herein, having different sizes.

The photothermal properties of hollow Au nanoparticles were also investigated using an infrared focal plane array camera (FUR model SC6000, 640×513 pixels, 25 μm pitch) with a detection window of 8-9.6 μm. The method compared the photothermal properties of two cuvettes containing two different nanoparticle suspensions: (1) solid spherical gold nanoparticles with a diameter of about 80 nm ($1.0 \times 10^{10}$ particles/mL) and (2) hollow gold nanoparticles with a cavity diameter of about 50 nm and an outer diameter of about 100 nm ($1.0 \times 10^{10}$ particles/mL). Each cuvette was placed at the focal plane of the camera lens, and collimated laser light (centered at 800 nm) was directed onto the center of the cuvette. The incident laser power was 350 mW, and the diameter of the collimated Gaussian beam was 3 mm. The incident light flux at the gold suspension was 1.2 W/cm$^2$. The image acquisition rate was 1 frame per second, beginning with the commencement of irradiation. The cuvettes were irradiated for 10 minutes each. Images were recorded for 30 minutes. To correlate temperature to measured infrared intensity for each image pixel, a calibration experiment was conducted. The calibration was carried out by recording images of a cuvette through which water was circulated from a heated water bath. A thermocouple placed in the water bath measured the temperature continuously in synchronization with the image acquisition. FIG. 29 shows the infrared absorbance image of the cuvette filled with hollow gold nanoparticles. The maximum temperature increase occurred at the center of the cuvette. Compared to the solid spherical gold nanoparticles, the temperature increase for the hollow gold nanoparticles was significantly enhanced, as shown in FIG. 30.

All patent documents referred to herein are incorporated by reference in their entireties. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A hollow metal nanoparticle comprising:
   a polycrystalline metal shell; and
   a cavity substantially defined by the shell,
   wherein:
   the shell has a thickness greater than or equal to about 5 nm;
   the shell has pores ranging in size from about 0.5 nm to about 3 nm disposed substantially the entire surface of the shell;
   the shell is formed from a plurality of grains having a grain size between about 3 nm and 8 nm;
   the cavity has a curved surface; and
   the nanoparticle has a surface roughness between about 3 nm and 8 nm.

2. The hollow metal nanoparticle of claim 1, wherein the cavity has a diameter of about 50 nm.

3. The hollow metal nanoparticle of claim 1, wherein the nanoparticle is substantially spherical and has a diameter of about 60 nm to about 150 nm.

4. The hollow metal nanoparticle of claim 1, wherein the shell has a thickness of about 8 nm to about 45 nm.

5. The hollow nanoparticle of claim 1, wherein the nanoparticle exhibits a surface plasmon resonance peak between about 600 nm and about 900 nm.

6. The hollow nanoparticle of claim 1, wherein the nanoparticle exhibits a surface plasmon resonance peak between about 600 nm and about 750 nm.

7. The hollow metal nanoparticle of claim 1, wherein the shell comprises Au.

8. The hollow metal nanoparticle of claim 1 further comprising at least one second nanoparticle at least partially disposed in the cavity defined by the metal shell.

9. The hollow metal nanoparticle of claim 8, wherein the at least one second nanoparticle comprises doped Fe$_3$O$_4$ comprising one or more of $^{64}$Cu, $^{89}$Zr, $^{11}$C, $^{18}$F, and $^{67}$Ga.

10. The hollow metal nanoparticle of claim 1, wherein the cavity comprises one or more of a gas, a nanoparticle, a therapeutic agent, an enzyme, a catalyst, and a dye.

11. The hollow metal nanoparticle of claim 1, wherein the cavity comprises a therapeutic agent.

12. The hollow metal nanoparticle of claim 1, wherein the nanoparticle further comprises one or more species associated with an outer surface of the nanoparticle.

13. The hollow metal nanoparticle of claim 12, wherein a first species associated with an outer surface comprises a Raman active species and forms a first layer and a second species associated with the outer surface comprises a polyethylene glycol moiety and forms a second layer, wherein the second layer substantially surrounds the first layer.

14. A composite particle comprising:
   at least one nanoparticle; and
   a polycrystalline metal shell substantially encapsulating the at least one nanoparticle and formed from a plurality of grains having a grain size between about 3 nm and 8 nm,
   wherein the metal shell has a thickness of about 10 nm to about 200 nm, a surface roughness between about 3 nm and about 8 nm, and pores ranging in size from about 0.5 nm to about 3 nm about substantially the entire surface of the shell, and wherein at least one surface of the at least one nanoparticle is not in contact with the shell.

15. A hollow metal nanoparticle comprising:
   a polycrystalline metal shell; and
   a cavity substantially defined by the shell,
   wherein:
   the shell has a thickness greater than or equal to about 5 nm;
   the shell is formed from a plurality of grains having a grain size between about 3 nm and 8 nm;
   the cavity has a curved surface and comprises a therapeutic agent within the cavity; and
   the nanoparticle has a surface roughness between about 3 nm and 8 nm about substantially the entire surface of the shell.

* * * * *